US012279807B2

(12) United States Patent
Truckai et al.

(10) Patent No.: US 12,279,807 B2
(45) Date of Patent: Apr. 22, 2025

(54) ANASTOMOSIS DEVICE AND METHOD

(71) Applicant: M. I. Advanced Thermosurgery, Inc., Hanover, NH (US)

(72) Inventors: Csaba Truckai, Saratoga, CA (US); Gergo Csikos, Budapest (HU); Viktor Mayer, Dunaharaszti (HU); Kornel Horvath, Budaörs (HU)

(73) Assignee: M. I. Advanced Thermosurgery, Inc., Hanover, NH (US)

( * ) Notice: Subject to any disclaimer, the term of this patent is extended or adjusted under 35 U.S.C. 154(b) by 0 days.

(21) Appl. No.: 18/350,622

(22) Filed: Jul. 11, 2023

(65) Prior Publication Data

US 2024/0156519 A1 May 16, 2024

Related U.S. Application Data

(63) Continuation of application No. 16/859,134, filed on Apr. 27, 2020, now Pat. No. 11,737,813.

(Continued)

(51) Int. Cl.
*A61B 18/14* (2006.01)
*A61B 17/11* (2006.01)
(Continued)

(52) U.S. Cl.
CPC .......... *A61B 18/1482* (2013.01); *A61B 17/11* (2013.01); *A61B 17/3205* (2013.01);
(Continued)

(58) Field of Classification Search
CPC . A61B 17/11; A61B 17/1114; A61B 17/3205; A61B 18/1482; A61B 2017/00398; A61B 2017/00477; A61B 2017/1132; A61B 2018/00619; A61B 2018/0072; A61B 2018/00791; A61B 2018/00869; A61B 2018/00875; A61B 2018/00892; A61B 2018/126; A61B 2090/061; A61B 2218/002; A61B 2218/007; A61B 2218/008

See application file for complete search history.

(56) References Cited

U.S. PATENT DOCUMENTS 3,057,355 A   10/1962  Smialowski et al.
4,573,468 A   3/1986   Conta et al.
(Continued)

FOREIGN PATENT DOCUMENTS

RU   2018269 C1   8/1994
RU   2217082 C2   11/2003
(Continued)

OTHER PUBLICATIONS

Chen; Investigation of Thermal Spread during Electrosurgical Coagulation in Neurosurgery; Doctoral dissertation; 99 pages; retrieved from the internet (https://deepblue.lib.umich.edu/bitstream/handle/2027.42/97905/krchen_1.pdf;sequence=1); 2013.

*Primary Examiner* — Tigist S Demie
(74) *Attorney, Agent, or Firm* — Shay Glenn LLP

(57) ABSTRACT

Methods and surgical devices for performing an anastomosis of a living tissue. More particularly the methods and devices relate to anastomosis of tissue performed through tissue fusion performed by delivering energy to the tissue.

12 Claims, 19 Drawing Sheets

Related U.S. Application Data

(60) Provisional application No. 62/845,449, filed on May 9, 2019, provisional application No. 62/838,694, filed on Apr. 25, 2019.

(51) Int. Cl.
    *A61B 17/3205*     (2006.01)
    *A61M 1/00*     (2006.01)
    *A61B 17/00*     (2006.01)
    *A61B 18/00*     (2006.01)
    *A61B 18/12*     (2006.01)

(52) U.S. Cl.
    CPC ... *A61M 1/774* (2021.05); *A61B 2017/00398* (2013.01); *A61B 2017/1132* (2013.01); *A61B 2018/0072* (2013.01); *A61B 2018/00869* (2013.01); *A61B 2018/00875* (2013.01); *A61B 2018/00892* (2013.01); *A61B 2018/126* (2013.01); *A61M 1/73* (2021.05)

(56) References Cited

U.S. PATENT DOCUMENTS

| | | |
|---|---|---|
| 4,917,090 A | 4/1990 | Berggren et al. |
| 5,222,963 A | 6/1993 | Brinkerhoff et al. |
| 5,250,058 A | 10/1993 | Miller et al. |
| 5,309,927 A | 5/1994 | Welch |
| 5,350,104 A | 9/1994 | Main et al. |
| 6,050,472 A | 4/2000 | Shibata |
| 6,524,322 B1 | 2/2003 | Berreklouw |
| 6,562,053 B2 | 5/2003 | Schulze |
| 6,575,985 B2 | 6/2003 | Knight et al. |
| 7,776,060 B2 | 8/2010 | Mooradian et al. |
| 8,303,610 B2 | 11/2012 | Schubert |
| 8,453,906 B2 | 6/2013 | Huang et al. |
| 8,770,460 B2 | 7/2014 | Belzer |
| 11,737,813 B2 | 8/2023 | Truckai et al. |
| 2002/0072761 A1 | 6/2002 | Abrams et al. |
| 2003/0004510 A1 | 1/2003 | Wham et al. |
| 2003/0216733 A1 | 11/2003 | McClurken et al. |
| 2005/0033278 A1 | 2/2005 | McClurken et al. |
| 2005/0043749 A1 | 2/2005 | Breton et al. |
| 2006/0064086 A1 | 3/2006 | Odom |
| 2007/0156139 A1 | 7/2007 | Schechter et al. |
| 2008/0195091 A1 | 8/2008 | Takashino et al. |
| 2009/0048589 A1 | 2/2009 | Takashino et al. |
| 2011/0152861 A1 | 6/2011 | Weisshaupt et al. |
| 2011/0301605 A1 | 12/2011 | Horner |
| 2012/0012636 A1 | 1/2012 | Beckman et al. |
| 2012/0101500 A1* | 4/2012 | Winter ............... A61B 17/1114 606/49 |
| 2012/0325893 A1 | 12/2012 | Pastorelli et al. |
| 2013/0035683 A1* | 2/2013 | Weisshaupt ........ A61B 17/0643 606/45 |
| 2014/0207135 A1 | 7/2014 | Winter |
| 2015/0080879 A1* | 3/2015 | Trees ................. A61B 18/1445 606/51 |
| 2015/0190134 A1 | 7/2015 | Weisshaupt et al. |
| 2017/0035421 A1 | 2/2017 | Marczyk |
| 2017/0071666 A1 | 3/2017 | Weisshaupt et al. |
| 2017/0224347 A1* | 8/2017 | Collins ............... A61B 17/068 |
| 2017/0238991 A1 | 8/2017 | Worrell et al. |
| 2019/0117287 A1 | 4/2019 | Nativ et al. |
| 2019/0183501 A1 | 6/2019 | Shelton, IV et al. |
| 2020/0315689 A1 | 10/2020 | Schneider et al. |

FOREIGN PATENT DOCUMENTS

| | | |
|---|---|---|
| RU | 2328992 C1 | 7/2008 |
| RU | 2364351 C1 | 8/2009 |
| WO | WO2020/220015 A1 | 1/2020 |
| WO | WO2020/225603 A1 | 11/2020 |

* cited by examiner

ANASTOMOSIS DEVICE AND METHOD

RELATED APPLICATIONS

This application is a continuation of U.S. application Ser. No. 16/859,134, filed Apr. 27, 2020, titled "ANASTOMOSIS DEVICE AND METHOD," which claims benefit of U.S. Provisional application Nos. 62/838,694 filed Apr. 25, 2019 and 62/845,449 filed May 5, 2019 each of which are incorporated by reference. This application is also related to PCT application PCT/US2020/030039 filed Apr. 27, 2020, the entirety of which is incorporated by reference herein.

FIELD OF THE INVENTION

The present invention relates to methods and surgical devices for performing an anastomosis of a living tissue. More particularly the methods and devices relate to anastomosis of tissue performed through tissue fusion performed by delivering energy to the tissue.

BACKGROUND OF THE INVENTION

Most traditional techniques for mechanically performing anastomosis of hollow organs involve the use of mechanical staplers that connect tissue edges of the dissected hollow organ by inserting metallic or plastic staples into the tissue. The need to perform anastomosis of tubular bodies can be found in gastric, esophageal, intestinal surgery and especially in vascular procedures. End to end anastomoses are generally performed by surgical staplers that deliver pairs of staggered rings of staples. The traditional process can also involve cutting the tissue with a circular knife blade to separate the tissue that is held within the circular ring. The separated tissue is then removed with the stapler to form a circular opening within the lumen along the stapling line.

In contrast to suturing tissue, electrosurgical tissue fusion can be used to join tissue without conventional sutures or in addition to suturing. The present disclosure includes methods and devices for performing an anastomosis using electrosurgical tissue fusion.

SUMMARY OF THE INVENTION

The present disclosure includes methods and devices for performing tissue fusion. The methods and devices can be suited for performing end-to-end anastomosis. In one example of such a device, the device includes an elongate shaft carrying a first clamping component and a second clamping component each respectively having a first tissue-engaging face and a second tissue-engaging face, the first tissue-engaging face and the second tissue-engaging face configured for clamping together a first end of a first tubular organ segment and a second end of a second tubular organ segment; a circular bi-polar electrode arrangement in at least of the first tissue-engaging face and the second tissue-engaging face, the circular bi-polar electrode arrangement configured to deliver energy from the energy source to thermally join the first end to the second end; and at least on aperture in at least one of the first tissue-engaging face and the second tissue-engaging face communicating with a flow channel in the shaft for providing inflows or outflow.

A variation of the device can further include a fluid source configured to provide fluid inflows through the flow channel and apertures to deliver fluid which facilitates release of welded tissue from the first tissue-engaging face and the second tissue-engaging face. The apertures can be disposed in both of the first tissue-engaging face and the second tissue-engaging face or only in one tissue engaging face.

In another variation, the surgical device includes a bi-polar electrode arrangement carried in both of the first tissue-engaging face and the second tissue-engaging face. The bi-polar electrode arrangement can comprise a plurality of spaced apart circular electrodes of opposing polarities.

The devices described herein can include an energy supply that comprises a controller and at least one electrical source for delivering current and where the bi-polar electrode arrangement is operatively connected to the controller and the at least one electrical source.

The controller can be adapted to sense at least one electrical parameter of current delivery consisting of impedance, capacitance and/or phase angle to sense the thickness of engaged tissue when the first and second clamping components engage tissue. In another variation, the controller is adapted to multiplex current delivery among various pairs of opposing polarity electrodes. The controller can be adapted to modulate current delivery to the bi-polar electrode arrangement in response to signals from at least one temperature sensor. Alternatively, controller can be adapted to sense at least one electrical parameter of current delivery consisting of impedance, capacitance and/or phase angle to sense an effective tissue weld. The controller can also terminate current delivery when a sensed electrical parameter indicates said effective tissue weld. Additional variations of the controller are adapted to deliver the fluid inflows from the fluid source after sensing an effective tissue weld. The controllers can deliver the fluid inflows for an interval ranging from 1 second to 60 seconds.

In another variation of the device, the device includes a motor drive configured to move the first clamping component and the second clamping component. The controller can be adapted to actuate the motor drive to move the first clamping component and the second clamping component at a variable rate. In additional variations, the controller is adapted to actuate the motor drive to move the first clamping component and the second clamping component at a first closing rate until the first clamping component and the second clamping component are spaced apart by a selected distance followed by a second closing rate to compress a tissue between the first clamping component and the second clamping component to a thickness of less than 0.5 mm (or any other range/distance as required). The controller can also stop the movement together of the first clamping component and the second clamping component when the thickness of the engaged tissue is within a preselected range. Additionally, or in the alternative, the controller stops the movement together of the first clamping component and the second clamping component controller when the controller senses at least one electrical parameter indicates the thickness of the tissue is within a preselected range. The controller can also actuate the motor drive to move apart the first clamping component and the second clamping component after the controller senses at least one electrical parameter indicating an effective tissue weld.

In an additional variation, the controller is adapted to actuate the motor drive to move apart the first clamping component and the second clamping component after a predetermined interval of delivering fluid inflows from the fluid source.

Controllers for use with the devices described herein can be adapted to actuate the motor drive to move apart the first clamping component and the second clamping component at variable speeds. Furthermore, the controller can be adapted slow or stop actuation of the motor drive to move apart the first clamping component and the second clamping component when the controller senses resistance to moving apart cause by tissue adhering to the bi-polar electrode arrangement. In an additional variation, the controller can be adapted to sense resistance moving apart the first clamping component and the second clamping component by sensing motor voltage. An additional variation of the controller allows for actuating the motor drive to move a circular cutting member axially from either the first clamping component and the second clamping component to excise tissue inwardly of the first tissue-engaging face and the second tissue-engaging face. The controller can also be adapted to actuate the motor drive to move the circular cutting member after the controller senses at least one electrical parameter that indicates an effective tissue weld.

Another variation of a surgical device for end-to-end anastomosis can include an elongate shaft carrying a first clamping component and a second clamping component each respectively having a first tissue-engaging face and a second tissue-engaging face, the first tissue-engaging face and the second tissue-engaging face configured for clamping together a first end of a first tubular organ segment and a second end of a second tubular organ segment; a circular bi-polar electrode arrangement in at least one of the first tissue-engaging face and the second tissue-engaging face, the circular bi-polar electrode arrangement configured to deliver energy from the energy source to thermally join the first end to the second end; and wherein the first tissue-engaging face and the second tissue-engaging face are oriented relative to the central axis at an angle ranging from 300 to 850.

In an additional variation, a surgical device for an end-to-end anastomosis of tubular organ segments includes an elongate member having a central axis carrying a first clamping component having a first tissue-engaging face; a second clamping component having a central shaft adapted for lockable coupling to the first clamping component, and having a second tissue-engaging face; an actuator mechanism coupled to the first clamping component and the second clamping component and configured to move the first clamping component and the second clamping component together so that the first tissue engaging face and the second tissue-engaging face clamp together respective ends of the tubular organ segments; electrodes in both the first tissue engaging face and the second tissue-engaging face; and at least one aperture in the first tissue engaging face and in the second tissue-engaging face communicating with a remote fluid source.

The fluid source can be configured to cause pulsed inflows through the at least one aperture. Alternatively, or in combination, the fluid source can be configured to cause non-pulsed inflows through the at least one aperture.

Variations of the device include the second clamping component having a flow pathway extending from the at least one aperture therein to a proximal end of the central shaft. In addition, a proximal end of the central shaft can include a connector for fluid-tight connection of the flow pathway to a flow channel in the elongate member that communicates with the fluid source. The second clamping component can include an electrical conductor extending from an electrode therein to a proximal end of the central shaft. The central shaft can also include a connector for coupling the electrical conductor with a cooperating electrical conductor in the elongate member that is adapted for connection to an electrical source. In an additional variation, the second clamping component includes a bore for receiving the central shaft, further including at least one sealing element for providing a fluid tight seal between the central shaft and the bore. The central shaft and bore can be configured with a key for causing the central shaft to be oriented in a selected rotational position when being coupled with the bore.

The present disclosure also includes a variation of a surgical device for end-to-end anastomosis comprising: an elongate shaft carrying a first clamping component and a second clamping component each respectively having a first tissue-engaging face and a second tissue-engaging face, the first tissue-engaging face and the second tissue-engaging face configured for clamping together a first end of a first tubular organ segment and a second end of a second tubular organ segment; a first electrode the first tissue-engaging face and a second electrode in the second tissue-engaging face, the first and the second electrode configured to deliver energy from an energy source to thermally join the first end to the second end; and a plurality of insulative projecting elements in at least one tissue-engaging face figure to prevent contact of an electrode in the first face with an electrode in the second face as the clamping components are approximated.

In another variation, the present disclosure includes methods of using an electrosurgical device for connecting tubular organ segments so as to communicate with one another. For example, such a method can include positioning the walls of a first tubular organ segment around a proximal face of a first clamp component of the device; positioning the walls of a second tubular organ segment around a distal face of a second clamp component of the device; moving together the first and second clamping components thereby clamping together walls of the first and second tubular organ segments; and delivering electrosurgical energy between the proximal and distal faces of the clamping components to thereby provide a circular thermal weld in the walls to connect the tubular organ segments.

The method can also include multiplexing energy delivery between a plurality of pairs of opposing polarity electrodes in the proximal and distal faces.

A variation of the method further comprises removing steam from the energy delivery site through a flow pathway in the device. The steam can escape passively through the flow pathway. Alternatively, or in combination, the steam can be extracted by a negative pressure source.

The method can also include excising tissue inwardly of the proximal and distal faces to thereby connect the lumens of the first and second tubular organ segments. Excising can be performed with a blade or an electrosurgical cutting element.

Another variation of a method of using an electrosurgical device for connecting tubular organ segments so as to communicate with one another, includes positioning the walls of a first tubular organ segment around an electrode-carrying face of a first clamp component, wherein the face is coated with a biocompatible fluid for preventing tissue adherence thereto; positioning the walls of a second tubular organ segment around an electrode carrying face of a second clamp component, wherein the face is coated with a biocompatible fluid for preventing tissue adherence thereto; moving together the first and second clamping components thereby clamping together walls of the first and second tubular organ segments; and delivering electrosurgical energy between the proximal and distal faces of the clamping components to thereby provide a circular thermal weld in the walls to connect the tubular organ segments.

DETAILED DESCRIPTION OF THE INVENTION

Figure 1:
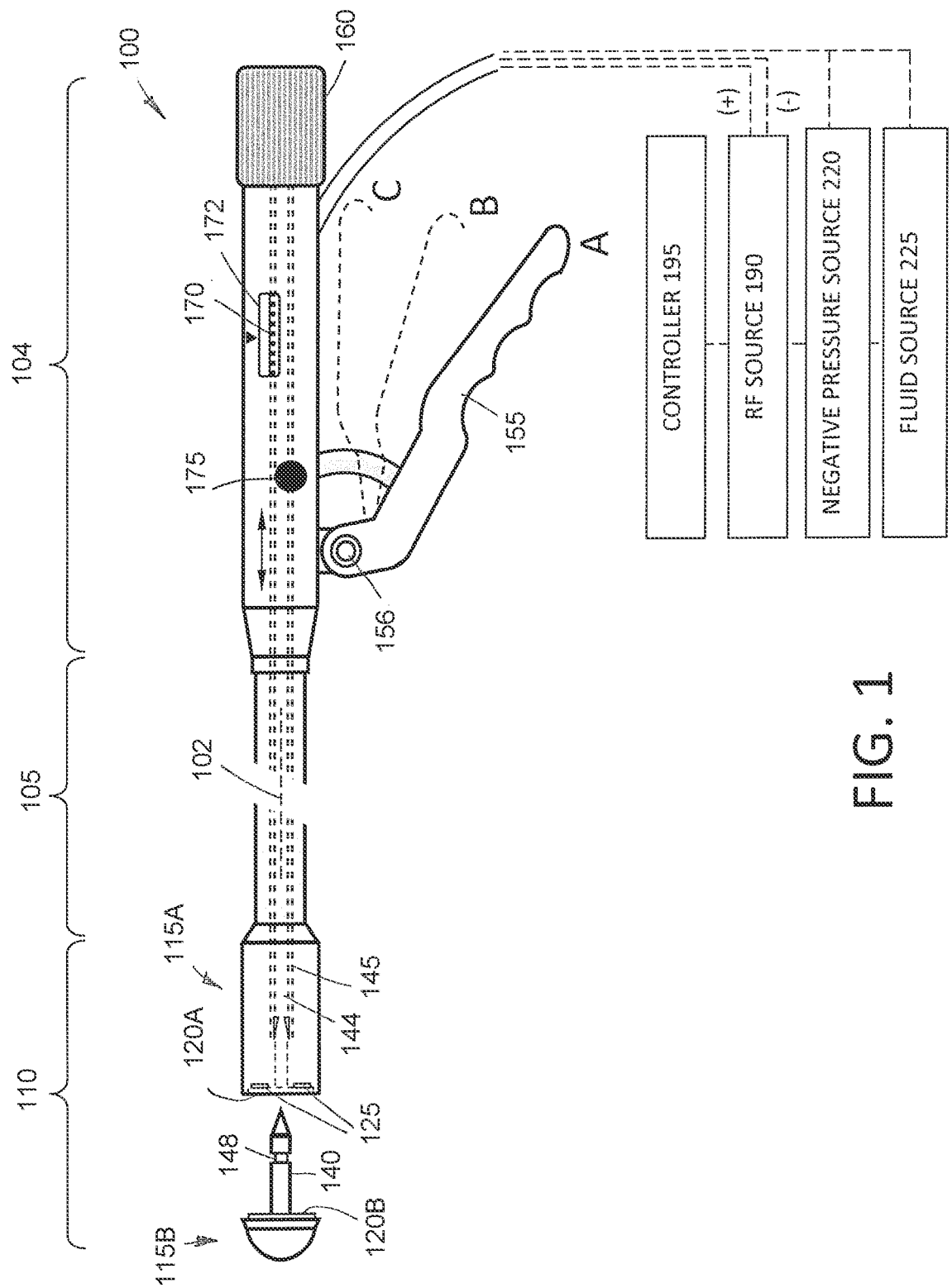
FIG. 1 is a side view of a surgical instrument corresponding to the invention illustrating a general overall view of the instrument.

FIG. 1 illustrates a circular anastomosis device 100 corresponding to the invention which is adapted for end-to-end connection of two segments of a hollow tubular body organ (e.g., two intestinal segments). In general, the anastomosis device 100 utilizes a clamping assembly and a bi-polar electrode arrangement adapted to create a circular thermal weld which surrounds a lumen or passageway between the connected organ segments. The device 100 further includes a circular knife for trimming excess tissue to connect and open the lumens of the two organ segments.

As can be seen in FIG. 1, the elongated anastomosis device 100 extends about a longitudinal axis 102 and includes an actuator handle portion 104, a longitudinal shaft assembly 105 and a working end consisting of a distal tissue-engaging assembly 110 which captures and clamps together tissue. The distal tissue-engaging assembly 110 or working end is further configured to apply energy from bi-polar electrode arrangement for thermally welding the tissue. The longitudinal shaft assembly 105 can have any suitable length and have a straight configuration, a curved configuration or can consist of a flexible shaft.

Figure 2:
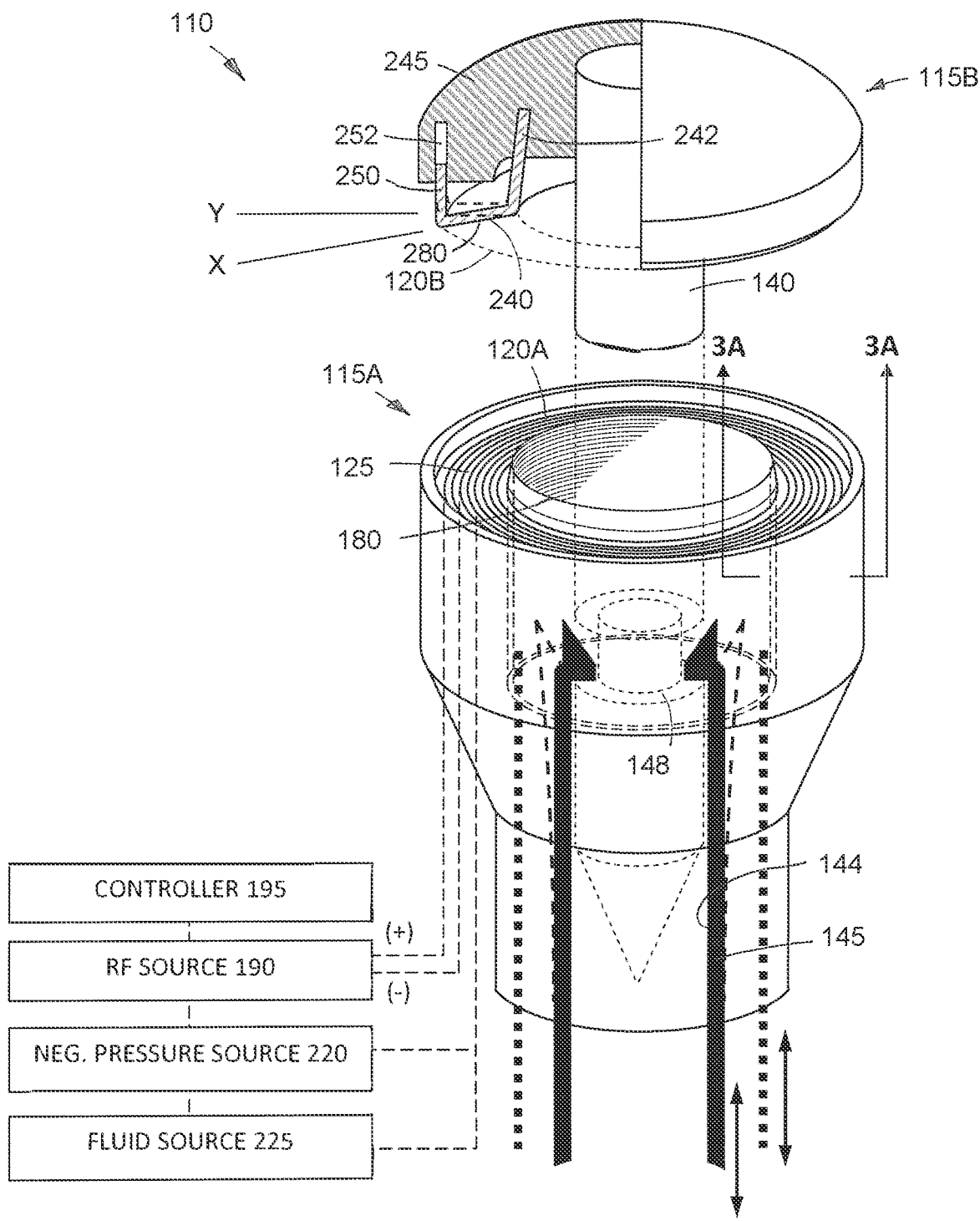
FIG. 2 is a perspective and cut-away view of the working end of the instrument of FIG. 1 showing the proximal and distal tissue engaging faces in a bi-polar electrode arrangement.

Referring to FIGS. 1 and 2, the distal tissue-engaging assembly 110 includes a proximal head or clamp assembly 115A and a mating distal head or clamp assembly 115B. The proximal clamp assembly 115A has a first tissue-engaging face 120A that faces distally and carries a bi-polar electrode arrangement 125 described in more detail below. The distal clamp assembly 115B has a second tissue engaging face 120B that faces proximally and opposes the bi-polar electrode arrangement 125. The first and second faces 120A and 120B are adapted to capture and engage tissue under very high compression forces as the proximal and distal clamp assemblies 115A and 115B are latched together and move toward one another.

In FIG. 1, it can be seen that the distal clamp assembly 115B has a proximally facing central trocar shaft 140 with an optional pointed trocar tip 142 which is adapted to longitudinally slide into a receiving channel 144 in a hollow support tube 145 carried in the proximal clamp assembly 115A. The distal clamp assembly 115B comprises an independent, detached component that is configured for placement in a tubular organ segment as is known in the art and will be described further below. The trocar shaft 140 includes an annular notch 148 which is engaged by opposing deflectable, spring-like retainer clips 150 carried at the distal end of the hollow support tube 145. The retainer clips 150 engage and latch into the annular notch 148 after the trocar shaft 140 is guided into the hollow support tube 140. To facilitate insertion of the trocar 140 into the channel 144, the trocar tip 142 has a low force profile which is provided by a taper at a selected angle to reduce the force required to bias open the retainer clips 150 (see FIG. 2). For example, the trocar tip 142 is configured with a conical shape to facilitate its insertion between the retainer clips 150. Such latching means are known in the art of circular anastomotic staplers and need not be described further here. Conventional circular anastomotic staplers with similar latching features include the following: U.S. Pat. Nos. 7,776,060; 5,350,104; 8,770,460; 5,222,963; 5,309,927 and 6,050,472.

As can be understood from FIGS. 1 and 2, the hollow tube 145 after latching to the trocar shaft 140 is configured for longitudinal movement to clamp together the first and second clamp assemblies 115A and 115B of the working end. As can be best seen in FIG. 1, the proximal handle portion 104 includes an actuator lever 155 adapted to move between positions A, B and C to actuate components of the working end of the device. In one variation, the lever 155 it is pivotally mounted by means of a pin 156 where movement of the lever from position A to position B moves the support tube 145, trocar 140 and the distal clamp assembly 115B in the proximal direction toward the proximal clamp assembly 115A. As can be understood from FIG. 2, movement of the support tube 145 in the proximal direction thereby moves the first and second tissue-engaging faces 120A and 120B toward one another to engage and compress tissue.

In one variation, a rotatable adjusting knob or grip 160 is provided at the proximal end of the handle assembly 104 that allows for additional adjustment of the spacing between the first and second tissue-engaging faces 120A and 120B. Thus, the movement of the lever 155 from position A to position B moves the clamp assemblies to clamp tissue and the rotatable knob or grip 160 allows for fine adjustment of thickness of tissue after being clamped together.

The gap between the tissue-engaging faces 120A and 120B (which is equivalent to engaged tissue thickness) is shown by a tissue thickness or gap indicator 170 in a window 172 in the handle portion 104. In one variation, the clamp assemblies are configured to compress the engaged tissue between the tissue-engaging faces 120A and 120B to a thickness ranging from 1.0 mm or a little as 0.2 mm.

Referring to FIG. 1, a lock button 175 is provided on the handle portion 104 for lock-release of lever 155 to allow its release to from position A to position B and thereafter from position B to position C. Movement of the lever 155 from position B to position C is adapted to advance a circular cutting blade 180 distally as will the described further below.

Figure 3A:
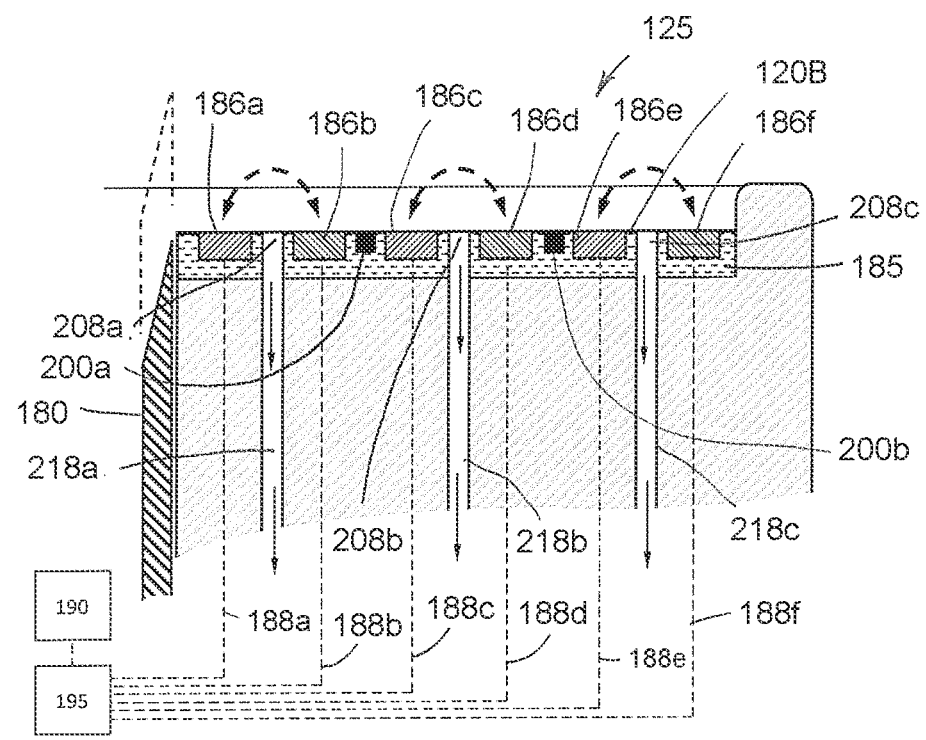
FIG. 3A is an enlarged sectional view taken line 3A-3A of FIG. 2 showing a portion of the bi-polar electrode arrangement of FIG. 1 and also showing multiplexed RF current delivery between adjacent pairs of electrodes.
Figure 3B:
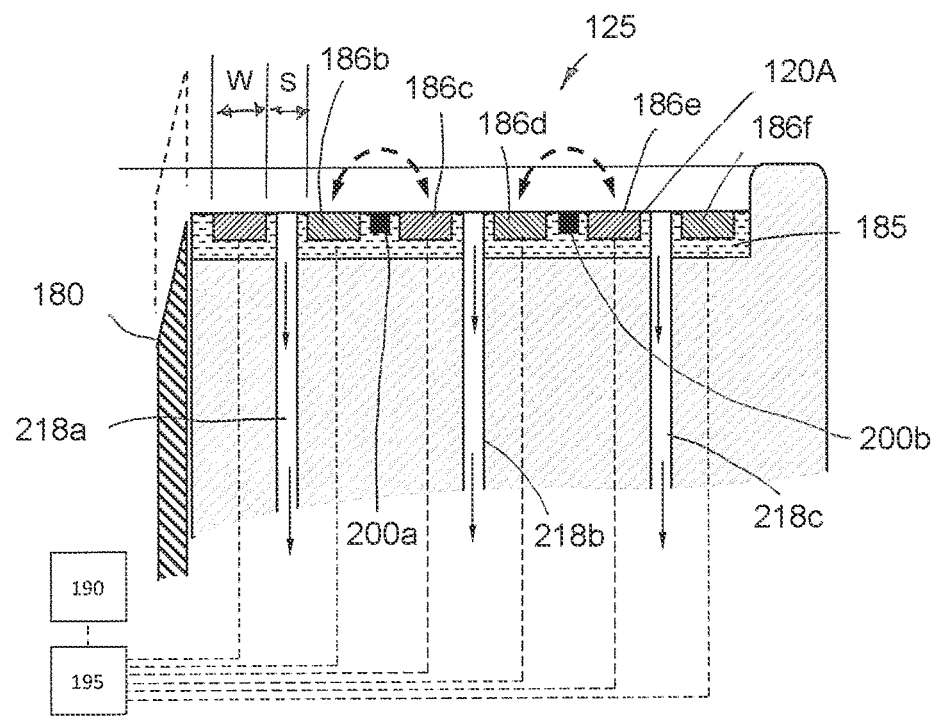
FIG. 3B is another view of the bi-polar electrode arrangement of FIG. 3A showing multiplexed RF current delivery between different pairs of adjacent electrodes.
Figure 3C:
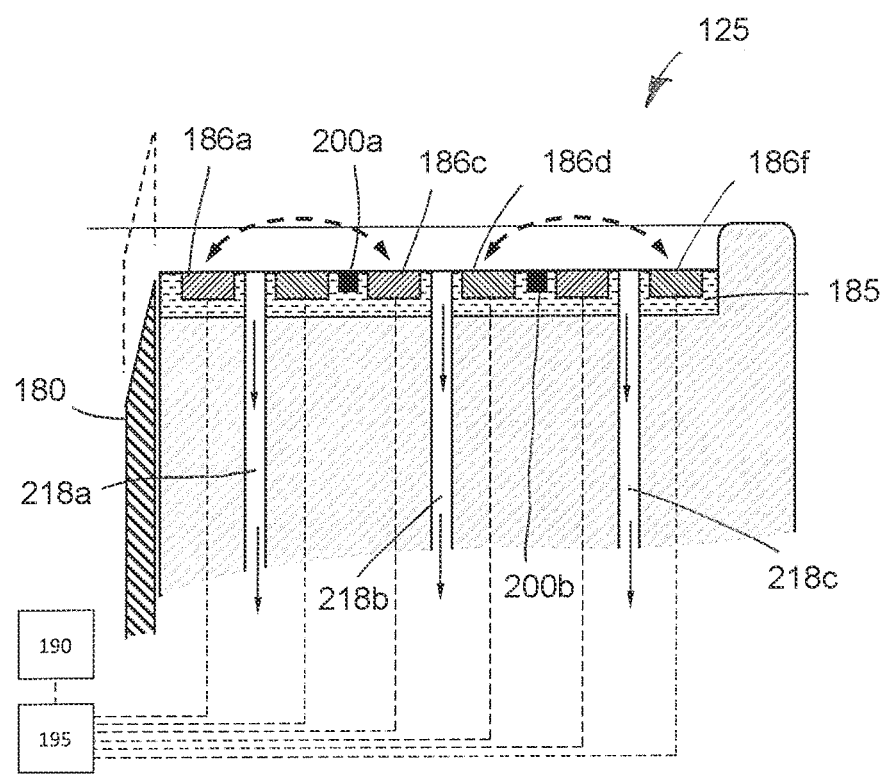
FIG. 3C is yet another view of the bi-polar electrode arrangement of FIGS. 3A-3B showing multiplexed RF current delivery between pairs of non-adjacent electrodes.

Now referring to FIG. 2, it can be seen that the bi-polar electrode arrangement 125 comprises a plurality of ring electrodes of opposing polarities that are adapted to deliver energy to tissue. As can be seen in FIGS. 3A-3C, the electrodes are disposed in a insulator substrate 185, which can be a ceramic, glass, the polymer or any combination thereof. In one variation, the electrodes can be a conductive metal carried in a flex circuit material which typically is Kapton® or a similar polymer. In another variation, conductive electrode rings can be carried in a silicone substrate.

In one variation, the number such ring electrodes can range from one pair of bi-polar electrodes to as many as 10 pairs of such bi-polar electrodes. Referring now to FIG. 3A, one side of the first tissue engaging face 120A is shown with six ring electrodes 186*a*-186*f*. Each ring electrode has a selected width W that cooperates with spacing S between such ring electrodes wherein the electrode width W and spacing S are important for delivering energy to tissue uniformly to thereby create an effective thermal weld. In general, the width W of an exposed electrode surface ranges between 0.1 mm and 2.0 mm and the spacing S between the ring electrodes ranges between 0.2 mm in 2.0 mm. As can further be seen in FIG. 2, the electrodes 186*a*-186*f* are coupled by separate electrical leads 188*a*-188*f* that extend through the shaft assembly 105 and handle portion 104 to an RF electrical source 190 and controller 195.

In general, the controller 195 is adapted to multiplex RF current flow between various pairs of bi-polar electrodes in a sequence. For example, in FIG. 3A, the controller 195 causes contemporaneous RF current flow through tissue (not shown) between electrode pair 186*a*-186*b*, electrode pair 186*c*-186*d* and electrode pair 186*e*-186*f*. In FIG. 3B, the controller 195 causes RF current to flow between electrode pair 186*b*-186*c* and electrode pair 186*d*-186*e*. In FIG. 3C, the controller 195 causes RF current to flow between electrode pair 186*a*-186*c* and electrode pair 186*d*-186*f*. In general, the controller 195 can provide for RF current flows between any paired electrodes, whether adjacent or non-adjacent.

In a first mode of operation, the controller 195 can multiplex between various pairs of electrodes in a preset sequence over a preset time interval. In a second mode of operation, the controller 195 can modulate energy delivery between any various pairs of electrodes in response to operational signals from such as impedance determined by the controller 195 for from signals from temperature sensors 200*a* and 200*b* in the working end of the device 100. FIG. 3A shows temperature sensors 200*a* and 200*b* in the tissue-engaging surface 120A intermediate the electrode rings, however the temperature sensors also can be positioned beneath one or more electrodes or in the distal tissue-engaging face 120B. When such temperature sensors are carried in the distal tissue-engaging face 120B, the electrical connections it can be provided by cabling and electrical connectors in the trocar 140 as can be easily understood.

Figure 4:
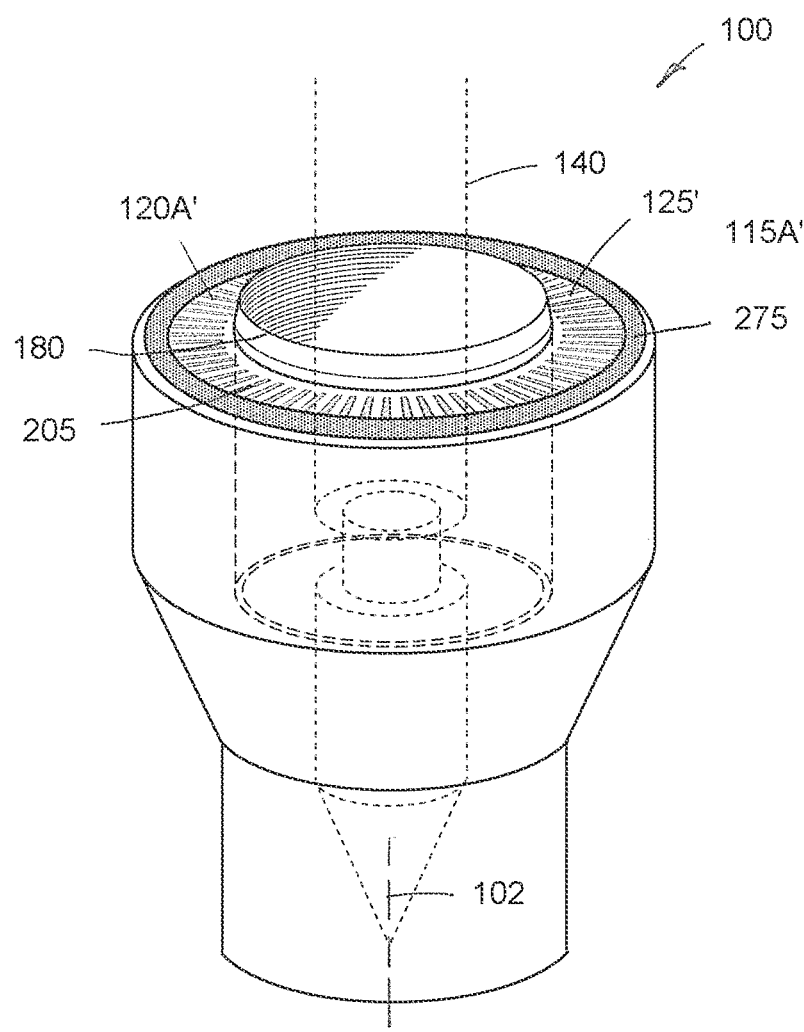
FIG. 4 is a perspective and cut-away view of another working end of an instrument similar to that of FIG. 2 illustrating a different variation of a bi-polar electrode arrangement.

While the circular bi-polar electrode arrangement 125 shown in FIG. 2 is typical, other generally circular electrode arrangements are possible. For example, FIG. 4 shows a proximal tissue-engaging face 120A' with a bi-polar electrode arrangement 125' comprising a plurality of electrodes 205 that are oriented radially relative to axis 102 of the device 100. In this variation, the controller 195 can multiplex energy delivery between various electrode pairs. It should be appreciated that other circular electrode arrangements possible, such as electrode dots, serpentine electrode pairs, etc.

Figure 5:
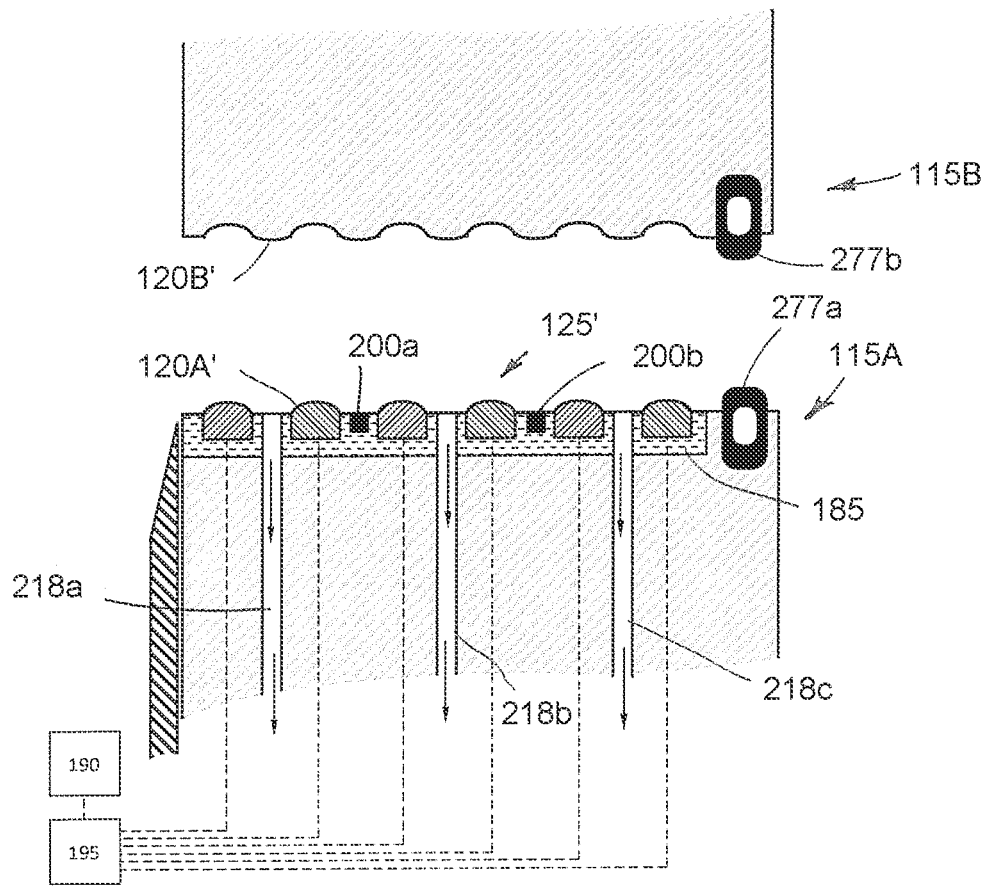
FIG. 5 is a sectional view of another bi-polar electrode arrangement similar to that of FIG. 3A illustrating ring electrodes with a smooth projecting surface for extracting tissue.

FIG. 5 illustrates another variation of bipolar electrode arrangement 125" wherein the opposing tissue engaging faces 120A' and 120B' have cooperating with undulating surfaces for compressing and stretching tissue. In this variation, the electrode surfaces are convex the project outwardly from the insulator substrate 185. It should be appreciated that a projecting and receiving teachers in opposing clamp surfaces can be used for stretching and compressing tissue which may assist in creating an effective tissue weld.

FIGS. 2 and 3A-3C illustrates another component of the invention which consists of mechanisms for extracting steam from heated tissue in the interface between the tissue-engaging faces 120A and 120B and tissue is welded with the bi-polar electrode arrangement 125. As can be seen in FIG. 3A, fluid flow ports 208a-208c are provided in the face 120A intermediate the electrodes 185a-186f. The ports 208a-208c are open to cooperating channels 218a-218c extending through the device which communicate with a negative pressure source 220 shown schematically in FIGS. 1 and 2. The number of locations of such ports in the first tissue-engaging face 120A can vary in number from 1 to 20 or more and can be distributed in any suitable manner around the face 120A. As will be described further below, the flow channels 218a-218c also can be used for infusing liquid from a fluid source 225 and into the tissue interface between the clamp assemblies following a welding procedure to assist releasing tissue from the clamping mechanism. In general, the electrodes in the proximal in distal faces 120A and 120B should comprise non-stick materials but infused saline can be used as a precautionary measure to ensure that tissue does not stick to the electrodes.

Figure 6A:
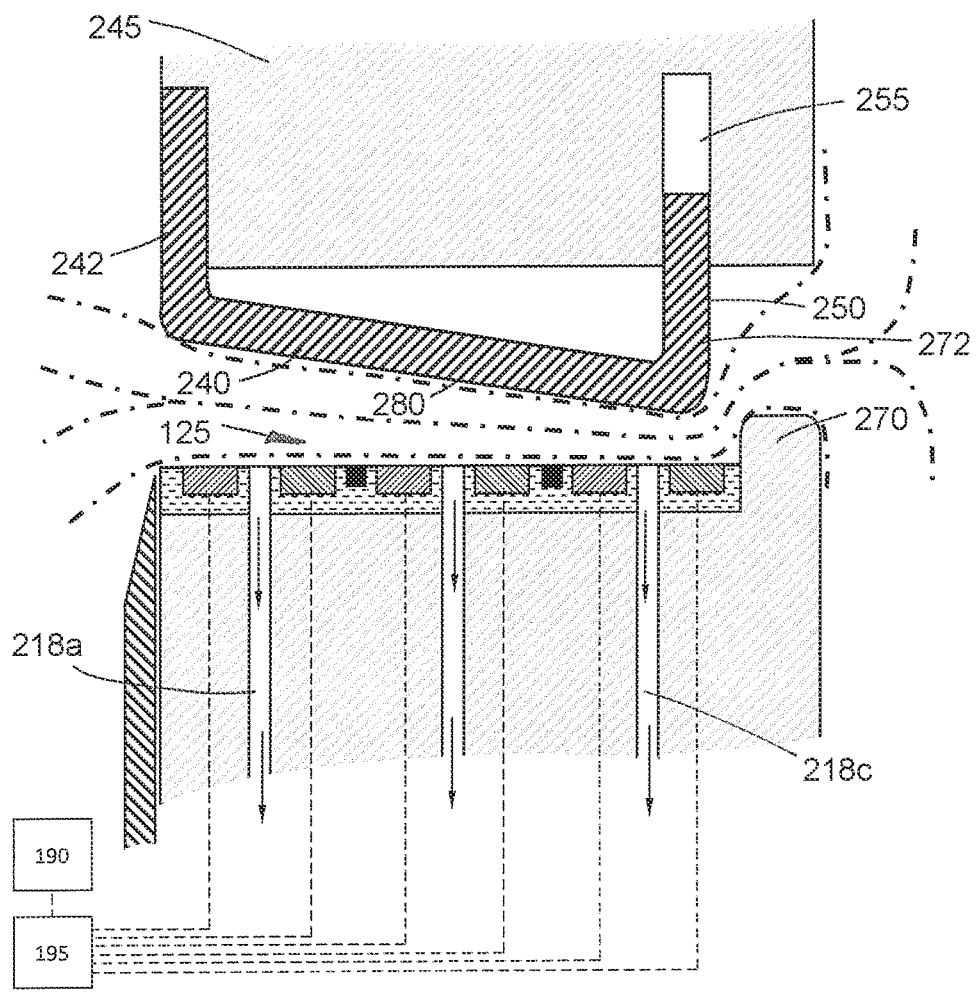
FIG. 6A is a view of the bi-polar electrode of FIG. 3A with a distal opposing face comprising flexing member that is adapted to progressively engage and compress tissue, with a flex member is shown initially engaging tissue at an outer periphery of the working end.
Figure 6B:
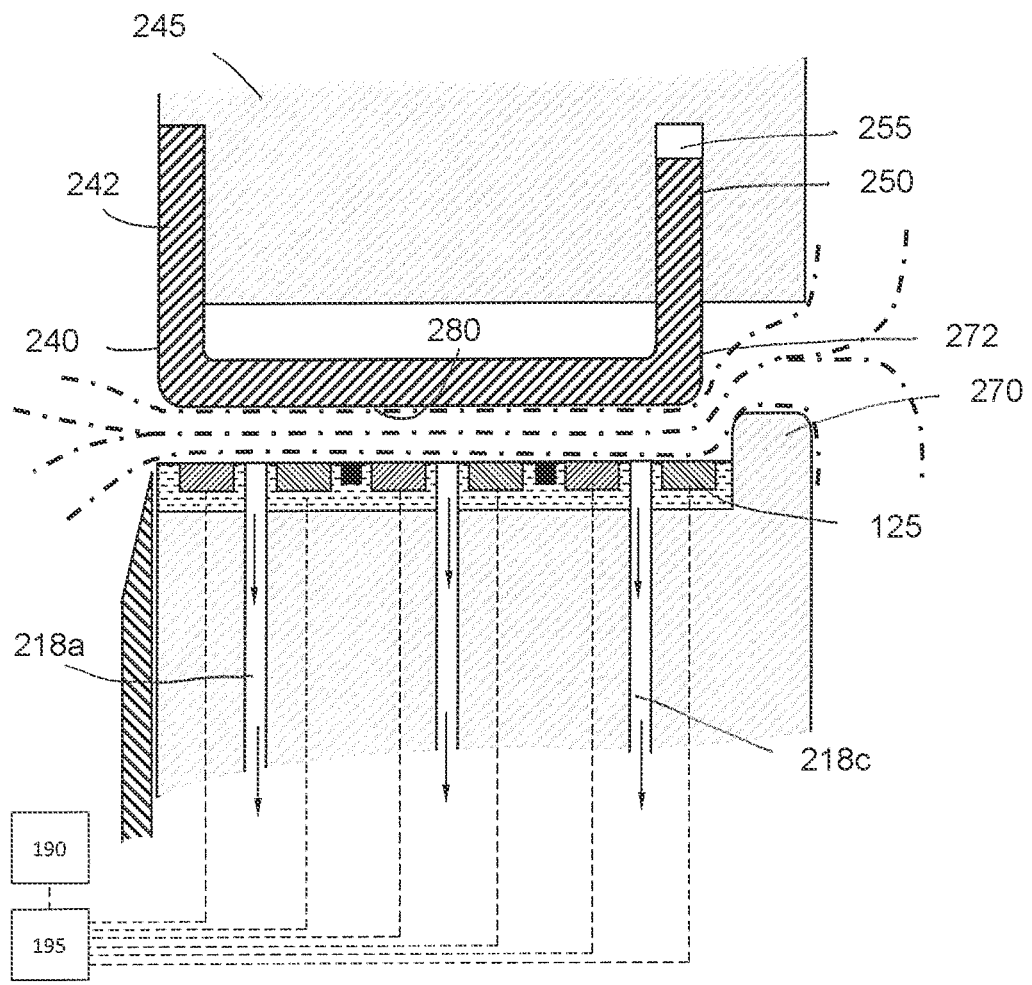
FIG. 6B is a view of the bi-polar electrode of FIG. 6A showing the flexing member progressively engaging tissue towards the center of the working end.

Referring to FIGS. 2 and 6A-6B, another aspect of the invention is shown wherein the distal tissue-engaging face 120B comprises a flexing member 240 with radially flexing surface that is adapted to progressively engage tissue that is clamped between the tissue-engaging faces 120A and 120B. As can be seen in FIGS. 2 and 6A, the flexing member 240 can comprise a spring-like metal form that is adapted to flex from a non-planar shape with surface angle X to a planar shape with surface angle Y which is perpendicular to axis 102 and parallel to the opposing proximal face 120A and the electrode arrangement 125. The function of the deflectable surface of the flexing member 240 is to initially engage tissue that is radially outward relative to central axis 102 of the device 100 and thereafter progressively compress the engaged tissue in the radially inward direction. Such progressive engagement of tissue is useful because the objective deliver energy to thermally weld the outer layers of the organ wall, without interference from fatty, inner surfaces of the intestinal wall. Thus, the progressive engagement the compression of the intestinal walls will squeeze and urge the fatty tissue and elemental radially inwardly and potentially inwardly from the region engaged by the bi-polar electrode arrangement 125. The outer membranes of the intestinal segments contain muscle tissue, connective tissue and the like which can be welded effectively.

In FIGS. 6A-6B, it can be seen that the distal tissue-engaging face 120 of the flexing member 240 is a circular surface slope at an angle X in a repose position. The circular inner edge 242 the flexing member 240 is secured to the body 245 of the distal clamp assembly 115B. The circular outer edge 250 of the flexing member 240 is adapted to move longitudinally into the circular slot 252 as the member is flexed. It should be appreciated that the flexing member in this variation can comprise a conductive metal material and can have various stent-type perforations arranged in the flexing member 240 to accommodate its movement and change of its surface shape from angle X to angle Y.

FIG. 6B shows the flexing member 240 entirely compressed against tissue in the opposing proximal tissue engaging face 120A which flattens the flexing member 240 to match the plane of the surface of the electrode arrangement 125.

In another aspect of the invention referring to FIGS. 2 and 6A, a variation of the proximal clamp assembly includes a lip or projecting edge 270 at the outer periphery of the proximal tissue engaging surface 120A that is adapted to overlap or engage opposing portion 272 of the distal clamp assembly to thereby limit steam from being expelled radially outwardly from the device during energy delivery. When delivering energy to tissue, it can be understood that the median desiccation tissue can cause steam formation, it is probable that any such steam being captured in the tissue and not released outwardly which could damage the organ segment outside the weld W. It should be appreciated that other features can perform a similar purpose such as flexible seals or O-rings on one or both of the radio outward edges of the clamp assemblies. For example, FIG. 4 shows an exemplary proximal clamp assembly 115A' with a flexible elastomeric seal 275 around the perimeter of the proximal tissue engaging face 120'. As another example, FIG. 5 shows cooperating elastomeric seals 277a and 277b in both tissue engaging faces 120A and 120B.

Figure 7E:
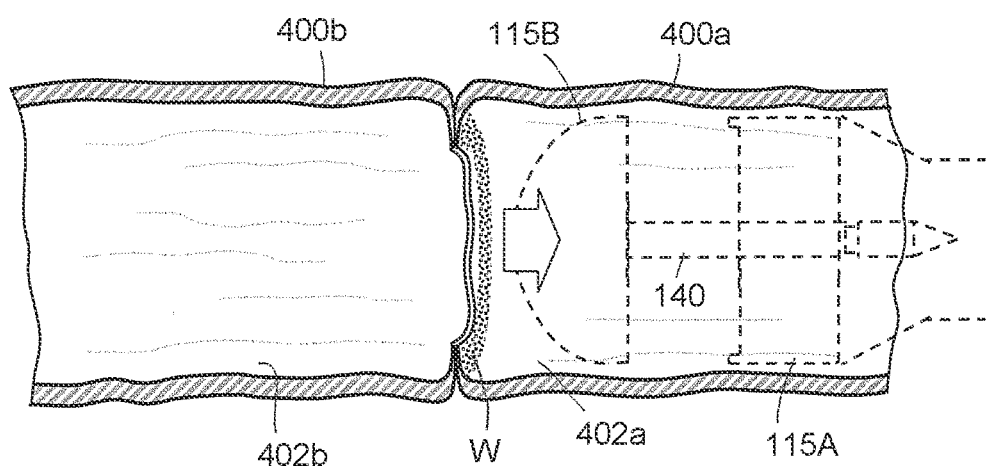
FIG. 7E illustrates a final step wherein the lever arm in the handle is actuated to release the clamping forces to disengage tissue and thereafter removal of the working end in the proximal direction.
Figure 8:
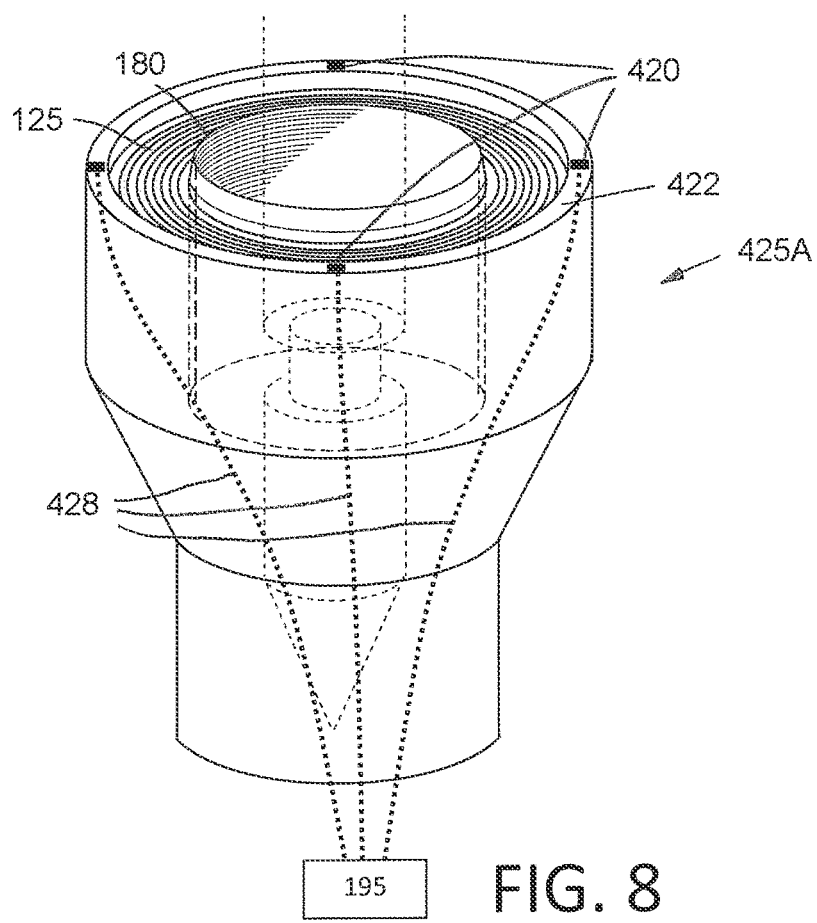
FIG. 8 is a perspective and schematic view of another clamp assembly of an instrument similar to that of FIGS. 2 and 4 illustrating pressure sensors that are configured to measure and signal tension on organ segments that are intended to be clamped together wherein in a significant tension is undesirable.

In another aspect of the invention referring to FIGS. 2 and 6A, the distal tissue-engaging face 120B comprises the flexing member 240 which is a conductive metal such as stainless steel and the surface as a passive electrode 280. Thus, RF current flow between pairs electrodes in the opposing proximal clamp surface 120A can be conducted through the engaged tissue and the passive electrode which may assist in creating an effective thermal weld W (FIG. 7E). In other variations, the tissue engaging surface 120B in the distal clamp assembly 115A can comprise in a nonconductive material. For example, FIG. 8 illustrates a tissue engaging surface 120B" that can consist of a monolithic block of elastomeric material, such as indent silicone or similar material, that is compressible to provide for progressive engagement above tissue as described previously in FIGS. 6A and 6B.

Referring again to FIG. 2, it also can be seen that the proximal clamp assembly 115A carries a circular cutting blade 180 that is adapted to move longitudinally to cut excess tissue radially inward from the circular electrode arrangement 125. In one variation, the circular blade 180 is actuated to move in the distal direction by the actuator lever the little left and 155 when moved from position B to position C as can be seen in FIG. 1.

Figure 9:
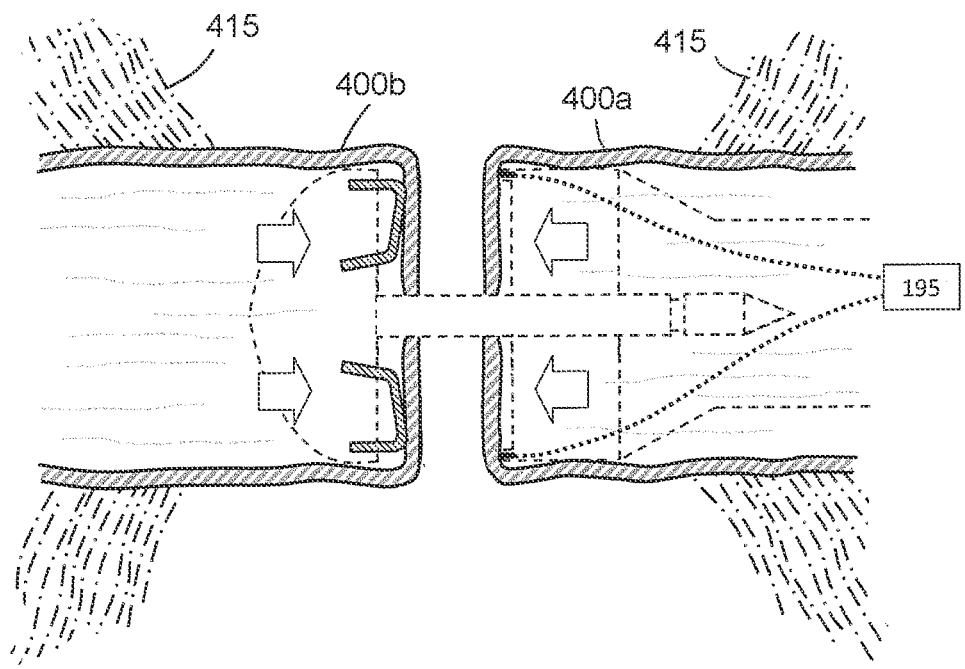
FIG. 9 illustrates another step of a method of the invention which comprises measuring the actual tension on the organ segments after coupling of the proximal and distal clamp assemblies.
Figure 10:
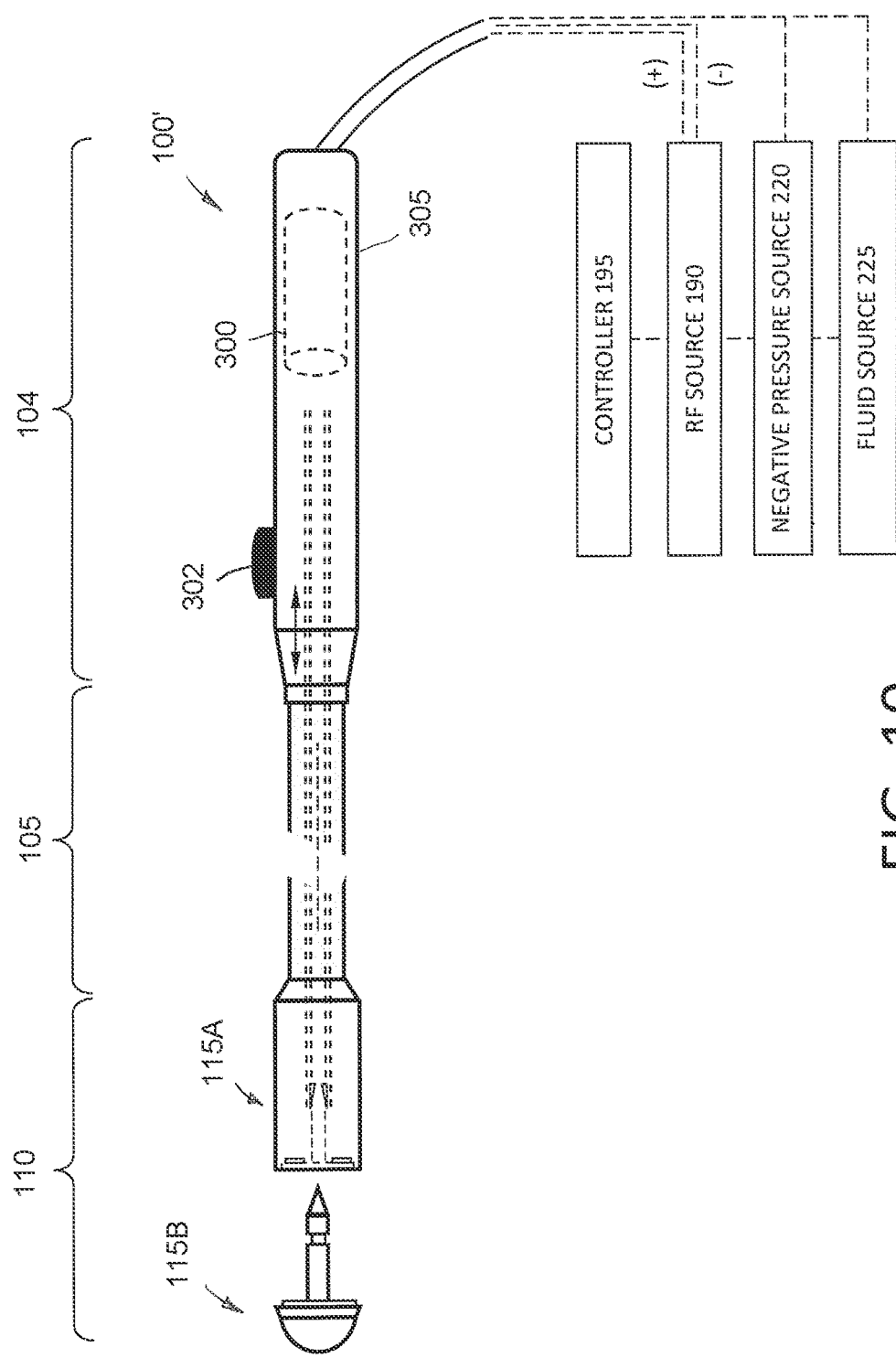
FIG. 10 is a side view of another variation of a surgical instrument similar to that of FIG. 1 except the device is motor driven to close the clamp assemblies.

Now turning to FIGS. 7A-7E, 8 and 9, methods using the device 100 of FIG. 1 or the device of FIG. 10 to connect tubular organ segments 400a and 400b is shown schematically. FIG. 10 illustrates a device 100' that is similar to the device of FIG. 1 except a motor 300 with actuator button 320 is provided in the handle body 305 to close and open the clamp assemblies and to actuate the circular cutting blade. In this variation, the controller 195 can control the speed of closure which can be responsive to sensed tissue parameters as described further below.

Figure 7A:
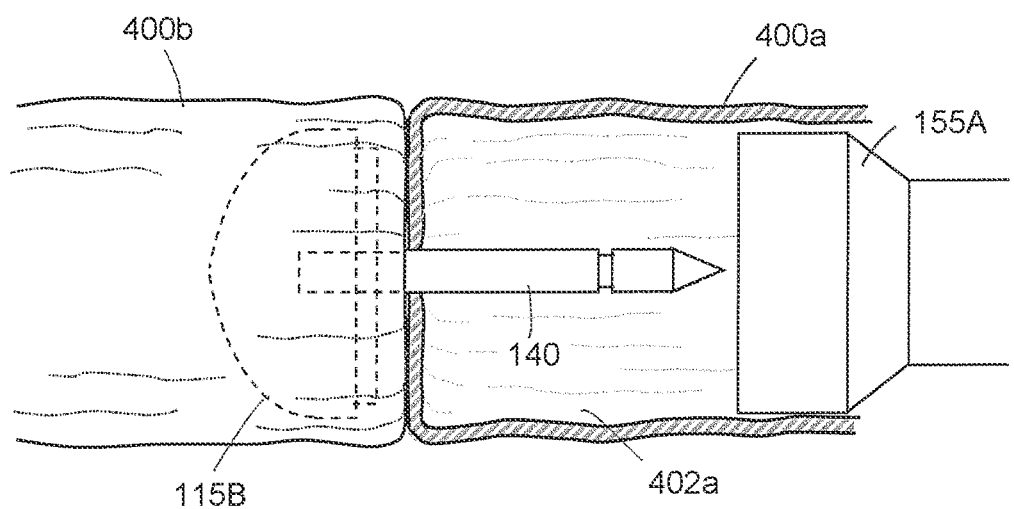
FIG. 7A illustrates a method of the invention for welding together to organ segments wherein an initial step includes positioning proximal clamp assembly in a first organ segment and a distal clamp assembly in a second organ segment.

In a typical application of joining two intestinal segments 400a and 400b together, the components are positioned in tissue organ segments as shown in FIG. 7A. The severed ends of organ segments 400a and 400b typically are secured with manually sewn, purse-string sutures. The proximal clamp assembly 115A is disposed in the lumen 402a of organ segment 400a. The distal clamp assembly 115B is disposed inside the lumen 402b of distal segment 400b and the trocar 140 then extends through the sutured end of the distal segment 400b.

Figure 7B:
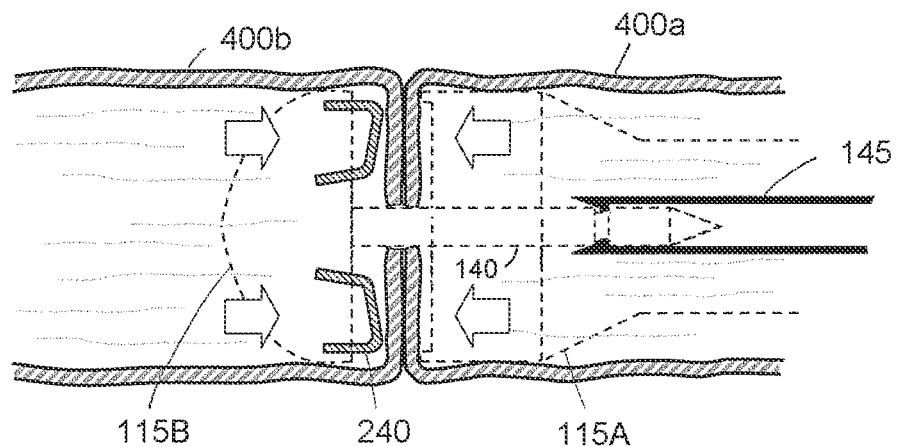
FIG. 7B illustrates a subsequent step of the method wherein the distal clamp assembly is latched into the proximal clamp assembly.
Figure 7C:
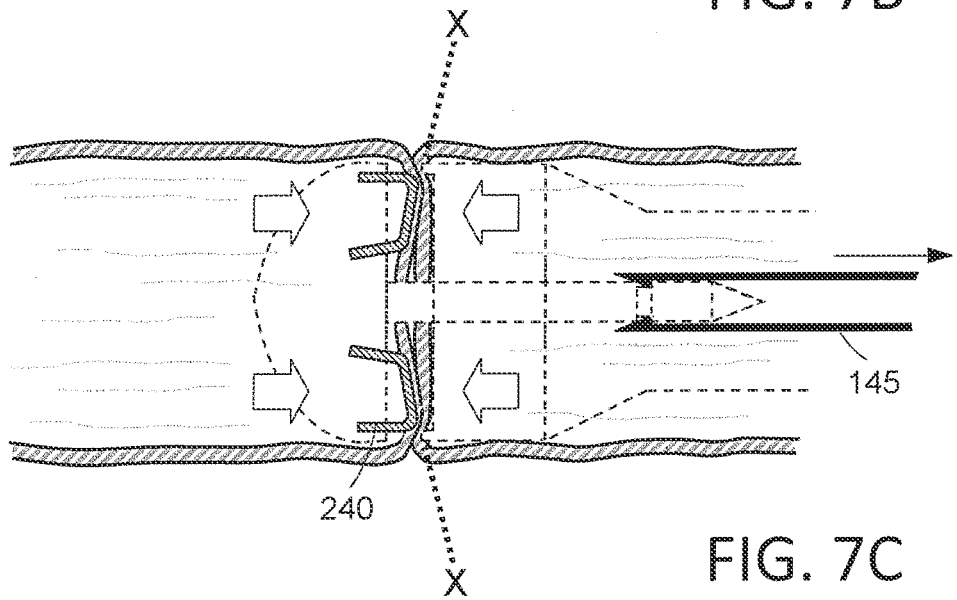
FIG. 7C illustrates a subsequent step wherein a lever arm in the handle is actuated to move the distal clamp assembly toward the proximal clamp assembly to engage tissue and wherein the flexing member of the distal clamp assembly progressively engages tissue.
Figure 7D:
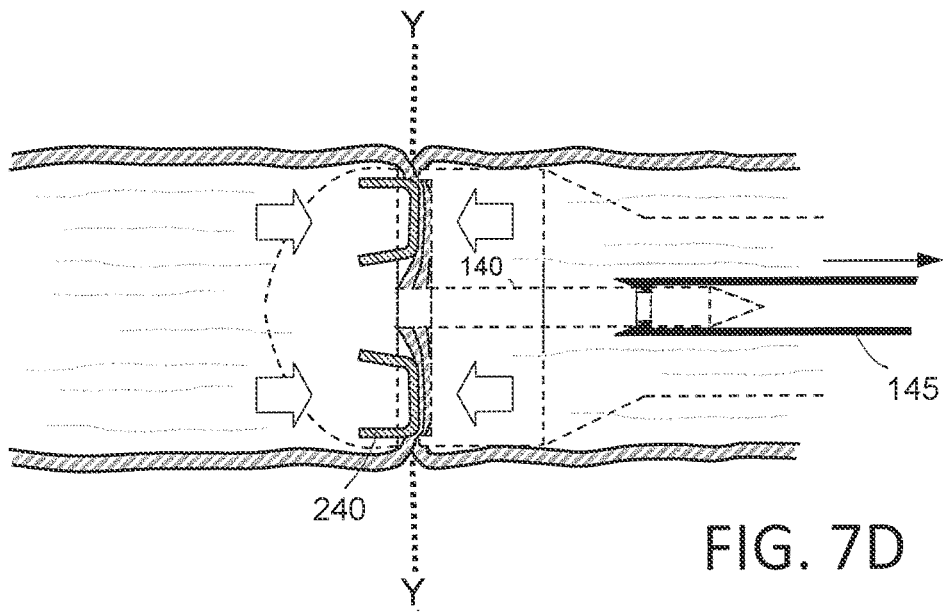
FIG. 7D illustrates a subsequent step wherein the lever arm in the handle is further actuated to cause the clamp assemblies to progressively engage tissue, followed by RF energy being delivered to weld together the organ segments, followed by actuating the cutting blade to cut and removed the tissue between the lumens of the organ segments.

As can be seen in FIG. 7B, the trocar 145 is then pushed longitudinally into the support tube 140 of the proximal clamp assembly 115A and latched therein as shown in FIG. 2. FIGS. 7B-7D schematically illustrate the progressive engagement of tissue by the first and second clamp assemblies 115A and 115B to thereby progressively compress together the engaged tissues. The tissue-engaging faces 120A and 120B initially compress tissue toward the outer periphery of the faces 120A and 120B and then progressively clamp tissue in the a radially inward direction as previously described above with reference to FIGS. 2, 6A and 6B.

In FIG. 7B, the distal clamp assembly is moved longitudinally to a position where the trocar 140 is locked into the proximal clamp assembly. FIG. 7C shows the distal clamp assembly 115A moved longitudinally to engage tissue which is caused by an initial movement of the actuator lever 155 from position A toward position B as shown in FIG. 1. As can be seen in FIG. 7C, the engagement face 100B is radially sloped at angle X relative to the flat surface of the first face 120A. Thereafter, FIG. 7B corresponds to the actuator lever 155 being moved to position B of FIG. 1 to thereby move the distal clamping face 120B toward the electrode arrangement 125 under high compression. Thus, in FIG. 7D, it can be seen that the opposing tissue-engaging faces 120A and 120B are parallel, with the face 120B flexed to angle Y, to compress the intestinal walls and engage the tissue against the electrode array 125.

Still referring to FIG. 7B, another step of a method of the invention includes clamping the tissue together until a predetermined tissue thickness is achieved. As described above, rotating the adjustment knob or grip 160 on the handle portion 104 is for fine control of the tissue thickness clamped between the proximal and distal clamp assemblies. The mechanical tissue thickness or gap indicator 170 in one variation can be used to determine the engaged tissue thickness.

In a variation, referring to FIGS. 7B-7C, a low level of electrical current can be delivered to the engaged tissue with the bipolar electrode array 125 or other dedicated electrodes as the clamping surfaces engage and compress the tissue. The term low-level current in this case means a level of electric current that does not heat or otherwise alter the structure of the tissue. The controller 195 then can contemporaneously sense and monitor an electrical parameter of the low-level current in the engaged tissue, for example impedance, capacitance and/or a phase angle of current in the engaged tissue. The controller 195 can carry a look-up table to determine if the sensed electrical parameter corresponds to a predetermined, known range of that particular electrical parameter which corresponds to a particular thickness of the engaged tissue. By this means, the controller 195 can determine the thickness of the engaged tissue. Further, the controller 195 can be adapted to multiplex current delivery among various electrode pairs and then determine if an average of the selected electrical parameter has been achieved to indicate the selected tissue thickness, or whether any tissue regions adjacent any energized electrode pair is too thick or too thin to be thermally welded effectively. In one variation, the low-level current can be pulsed, with power in the range of 2 W to 5 W and a pulse interval in the range of 1 to 25 milliseconds every 50 to 250 milliseconds. When using the motor-driven closing feature of the embodiment of FIG. 10, the initial closure rate of the central shaft can be from 5 cm/min to 50 cm/min and more often from 10 cm/min to 25 cm/min. When the clamp faces are a selected distance apart, for example from 1 mm to 2 mm, then the closing speed changes for the final closure to the range of 2 to 4 mm/min. Contemporaneous with the final closing speed, the controller can sense the electrical parameters of the low-level current described above, and stop the closure when the selected electrical parameter is achieved. Typically, the clamp faces compress the engaged tissue to a thickness of 0.10 mm to 0.30 mm wherein one electrical parameter can be impedance in the range is 5-20 ohms.

When closing the clamp faces manually with the device 100 of FIG. 1, the closing can be continued with rotation of knob or grip 160 until the controller 195 signals that the selected electrical parameter has been achieved.

A visual or aural signal can be provided to indicate to the physician that the engaged tissue is in a predetermined acceptable thickness range. In one variation, the controller 195 can include a locking mechanism that prevents RF energy delivery if the tissue thickness is not in the selected range.

Now referring to FIG. 7D, the physician then activates the RF source 190 and controller 195 to multiplex RF energy delivery as described above to thereby weld the intestinal walls together. In one variation, RF energy is delivered over an interval during which the controller 195 calculates tissue impedance with the bi-polar electrode array and a controller algorithm is adapted to modulate and/or terminate RF energy delivery after a predetermined impedance parameter is reached which indicates that an effective tissue weld has been formed. Such impedance can be calculated continuously as RF energy is multiplexed between various electrodes pairs as the tissue is welded. In one variation, such a predetermined impedance parameter can consist of an average impedance among RF energy delivery to various electrode pairs. In another variation, the controller can terminate RF energy delivery to any first pair of electrodes where a predetermined impedance parameter is reached, while delivering RF energy to any other electrode pairs, with RF energy delivery terminated at each such other pair when the predetermined impedance parameter is reached. It should be appreciated that other electrical parameters, such as capacitance, can be used in place of or in addition to an impedance parameter which are indicative of an effective weld to control RF energy delivery.

In another variation, the system may include different types of sensors for determining whether the tissue weld is affected in the fluid type. For example, light transmission from an LED in the working end can be transmitted through the welded tissue and one or more locations in the sensor can sense transmitted light to determine whether the tissue weld is effective. In this variation, it can be understood that welded tissue as substantially different characteristics for light transmission therethrough than native tissue.

Following the welding of organ segments 400a and 400b, the physician then actuates the lever arm 155 from position B to position C (see FIG. 1) to thereby advance the circular cutting blade 180 in the distal direction to cut and remove tissue inward of the circular weld W (FIG. 7E) thereby providing an opening between the lumens 402a and 402b of the two organ segments 400a and 400b. The excess tissue cut away by the cutting blade 180 remains secured to the trocar 140 so that such tissue is removed with the instrument.

Thereafter, the lever arm 155 is moved from position C back to position A to thereby move apart the distal and proximal clamp assemblies 115A and 115B so that tissue is no longer clamped by the working end 110. Then, as can be seen in FIG. 7E, the device 100 and working end 110 is moved proximally and withdrawn from the organ lumens. As can be seen in FIG. 7E, the weld W then provides a fluid-tight connection between the organ segments. When using the motor-driven device of FIG. 10, the motor can be actuated in reverse to open the clamping assemblies.

Figure 11:
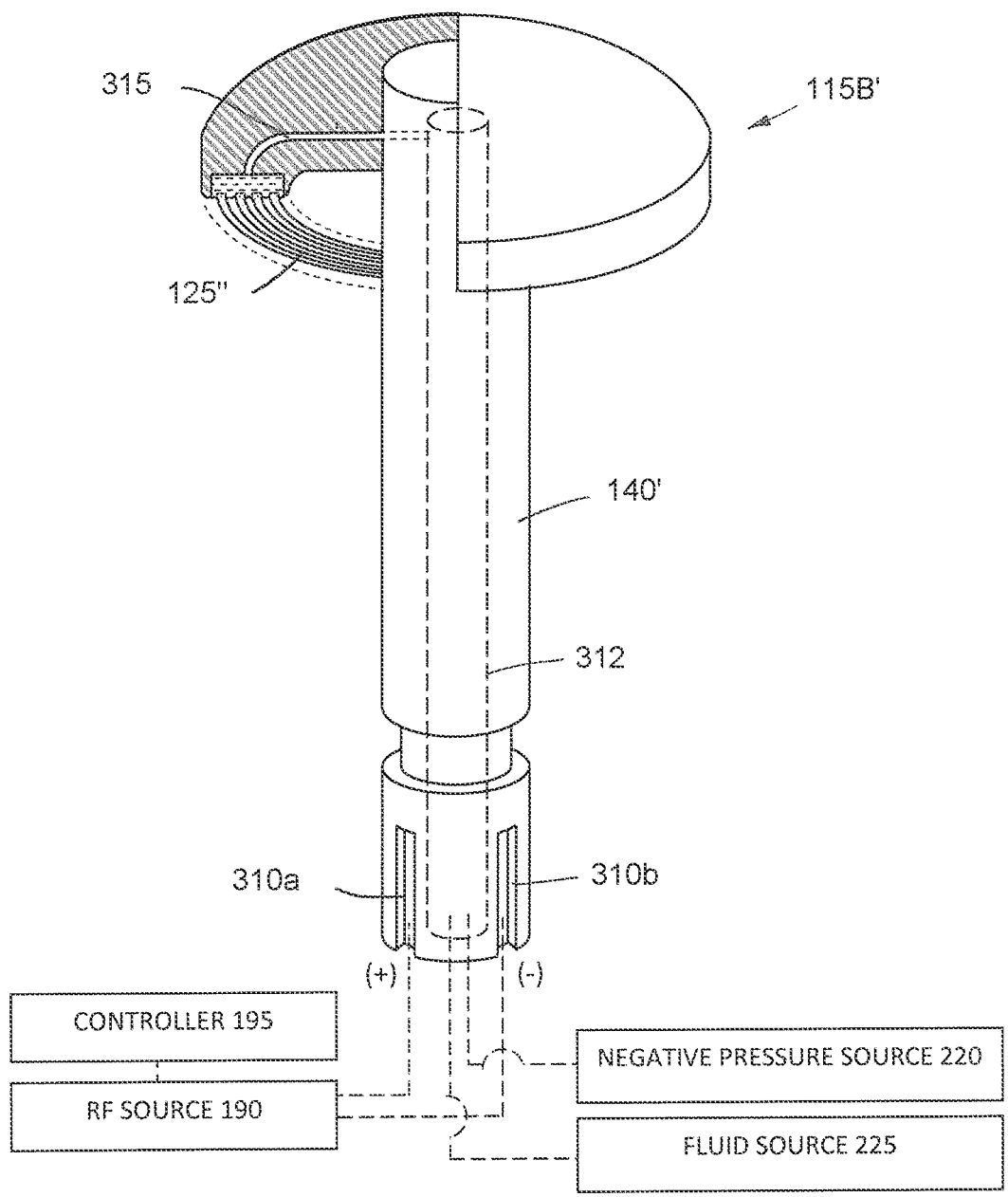
FIG. 11 is a perspective cutaway view of an alternative distal clamp assembly similar to that of FIG. 2 except new variation carries an electrode array as well as fluid flow channels similar to those features as described in FIG. 2-6B in the proximal clamp assembly.

In the embodiments described above, the electrode arrangement 125 is carried in the proximal clamp assembly 115A, but it is also possible to position the bi-polar electrode arrangement in the distal clamping assembly or with opposing polarity electrodes in both proximal and distal clamp assemblies 115A and 115B with FIG. 11 illustrating a variation of distal clamp assembly 115B'. In such a configuration where the distal clamp assembly 115B' carries such an electrode array 125", electrical cabling from the RF source 190 to the distal clamp assembly 115B' is be carried in the interior of the trocar 140' following its connection to the proximal clamp assembly 115A. The trocar 140' can carry electrical connectors 310a and 310b as shown in FIG. 11. As also shown in FIG. 11, the trocar 140' can include an interior passageway 312 extending therethrough with flow channels 314 extending to the electrode array 125" with the interior passageway 312 coupled to the negative pressure source 220 and the fluid source 225 to function as described previously delivering fluid flows to them from electrode array 125" during and/or after the tissue welding step.

In any variation of clamping assemblies, energy delivery for tissue welding can be provided by resistive heating elements, inductive heating elements, ultrasound transducers, light energy emitters and the like. Further, a circular stapling mechanism can be provided in the clamping assemblies as is known in the art in combination with the thermal welding mechanism described above.

Now referring to FIGS. 8 and 9, another component and related method of the invention is illustrated which is adapted for sensing the tension on the organ segments 400a and 400b prior to the treatment steps described above. It can be understood that the organ segments 400a and 400b must be mobilized or dissected away from connective tissue 415 following a procedure which resects a portion of an intestine. Depending on the length of intestine segment removed, it may be necessary to dissect a significant amount of momentum and other connective tissues 415 away from remaining segments 400a and 400b in order to eliminate unwanted axial tension on the organ segments after being connected. In an open surgical procedure, it may not be difficult to mobilize the organ segments manually so that there is no tension on the organ segments. However, in a laparoscopic procedure, it is difficult to sense whether the organs are under such unwanted tension. If there remains axial tension on the connected organ segments, it could potentially stress or damage the weld. In FIG. 8, it can be seen that pressure sensors 420 are positioned around an edge 422 of the proximal clamp assembly 425A. Any number of such pressure sensors 420 can be provided, for example, from 1 to 10, with 4 such sensors shown in FIG. 8. The sensors 420 can be any type of sensitive pressure sensor that is known in the art such as electronic pressure sensor. In one variation, a plurality of force sensor resistors (FSRs) can be used to measure tension wherein such sensor are resistors that changes in resistive value in ohms in response to pressure on the resistive element. Such sensors 420 are low cost and can be used in a combination around the perimeter 422 of the clamp assembly 425A to determine such tension.

In FIGS. 8 and 9, it can be seen the sensors 420 are connected to the controller 195 with electrical cabling 428 that can send electrical current to the sensor to thereby allow the controller to monitor impedance or another electrical parameter such as capacitance or phase angle. In one variation, the controller 195 can average the pressure sensed among the plurality of sensors 420 and provide a visual indication on a screen on the controller 195 that indicates the axial tension on the organ segments 400a and 400b. In one variation, the controller 195 can prevent RF energy delivery for welding the organ segments if the tension exceeds a predetermined value. In this variation, the tension on the organ segments 400a and 400b can be measured and displayed on the controller 195 continuously during the step of coupling the proximal and distal clamp assemblies together and thereafter closing together the clamp assemblies to approximate the proximal and distal segments 400a and 400b before RF energy is delivered to weld the tissue.

While it should be appreciated that plurality of pressure sensors 420 are shown in the proximal clamp assembly 425A, one or more pressure sensors also could be carried in the distal clamp assembly (see. FIG. 2) and coupled to the controller 195 through cabling in the trocar 140. In another variation, one or more sensors 420 in the interior of the proximal clamp assembly can be configured to measure tension on the trocar after the proximal and distal clamp assemblies are locked together.

Figure 12:
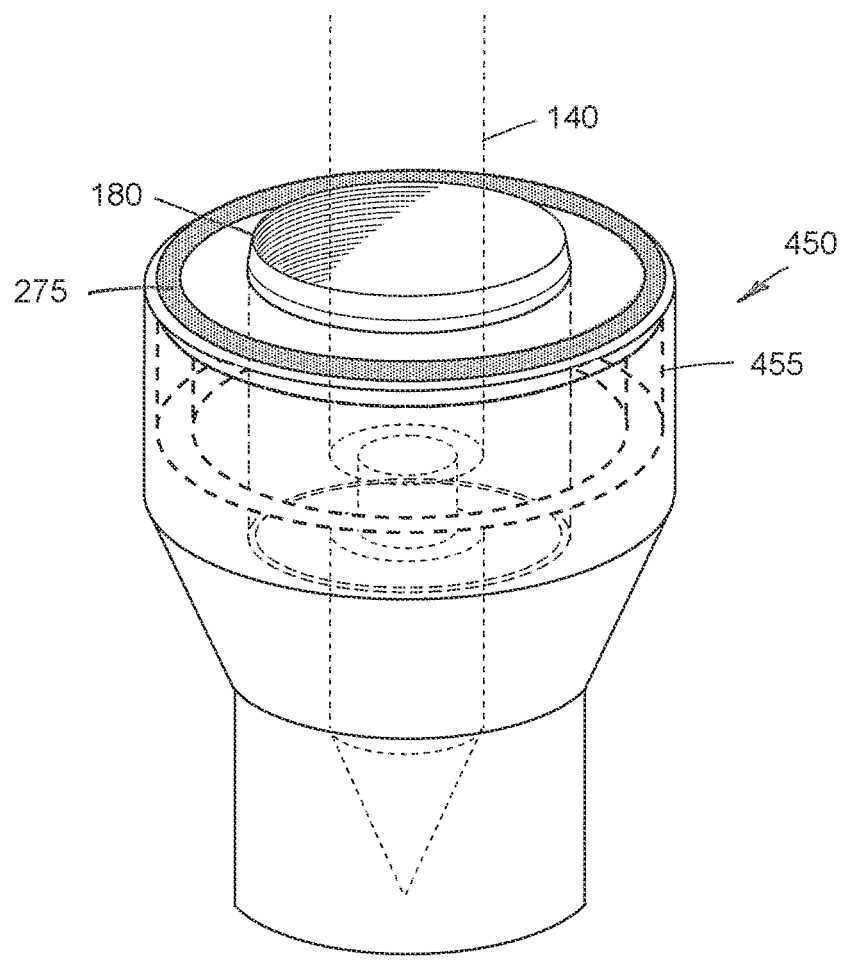
FIG. 12 is a perspective and schematic view of another clamp assembly of an instrument similar to that of FIGS. 2 and 4 illustrating a cooling mechanism in the clamp assembly for cooling tissues to thereby prevent damage to tissues outside of the targeted welding zone.

FIG. 12 illustrates another variation of the proximal clamp assembly 450 that is similar to that of FIG. 4 with an additional tissue cooling subsystem 455 added to the component. In this variation, the cooling subsystem 455 is provided to cool tissue in contact with the clamp assembly 450 outwardly from the zone of weld tissue (See FIG. 7E). It can be important to prevent any thermal damage to the organ segments outward from the weld. In one variation, subsystem 455 comprises one or more a Peltier elements adapted to cool the entire proximal clamp assembly 115A. In another variation, the subsystem 455 comprises or includes a heat sink fabricated of any suitable materials that are highly thermally conductive, for example, a conductive metal such as copper or a similar highly conductive material. In another variation, the tissue cooling subsystem can comprise an active cooling system where a cooling fluid flows through flow channels are provided, for example, with fluid flow provided by a motor driven pump carried in the handle portion. Alternatively, a cryogenic fluid can be released from a canister in the handle to flow through channels to cool the clamp assembly. In other variations, the tissue cooling subsystem mechanism can comprise or include a heat pipe extending into the handle as is known in the art. All of the above cooling mechanisms also can be provided in the distal clamp assembly 115B (see FIG. 2) with electrical connections and/or flow channels in the trocar 140' as shown in FIG. 11.

Figure 13:
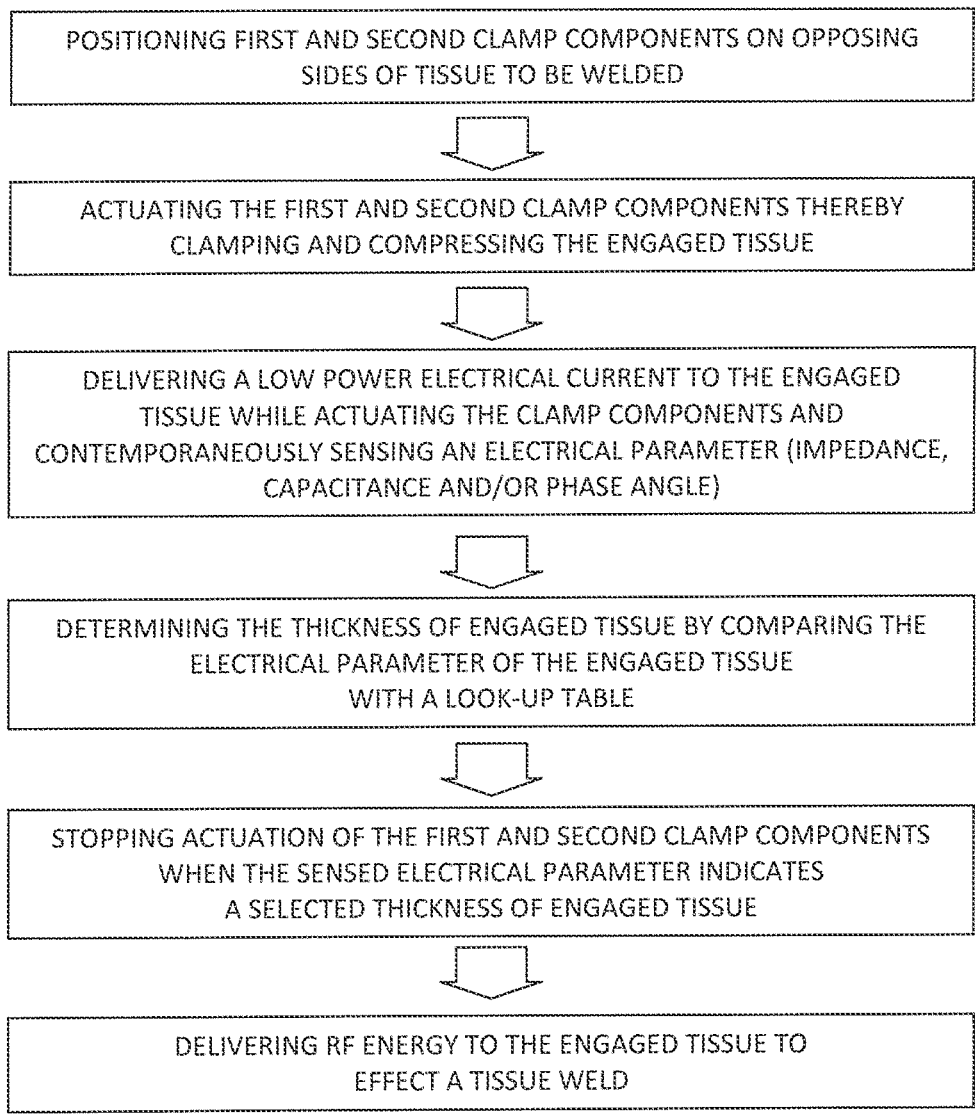
FIG. 13 is a diagram illustrating the steps of a method corresponding to the invention to determine the thickness of engaged tissue and to thereafter thermally weld together tubular organ segments.

In general, a method corresponding to the invention shown in FIG. 13 comprises (i) positioning first and second clamp components on opposing sides of tissue to be thermally welded, (ii) actuating the first and second clamp components thereby clamping and compressing the engaged tissue, (iii) delivering a low-power electrical current to the engaged tissue while actuating the clamp components and contemporaneously sensing an electrical parameter which can be impedance, capacitance and/or phase angle, (iv) determining the thickness of the engaged tissue by comparing the electrical parameter of the engaged tissue with a look-up table, (v) stopping actuation of the first and second clamp components when the sensed electrical parameter indicates a selected thickness of the engaged tissue, and (vi) delivering RF energy to the engaged tissue to effect a tissue weld.

Figure 14:
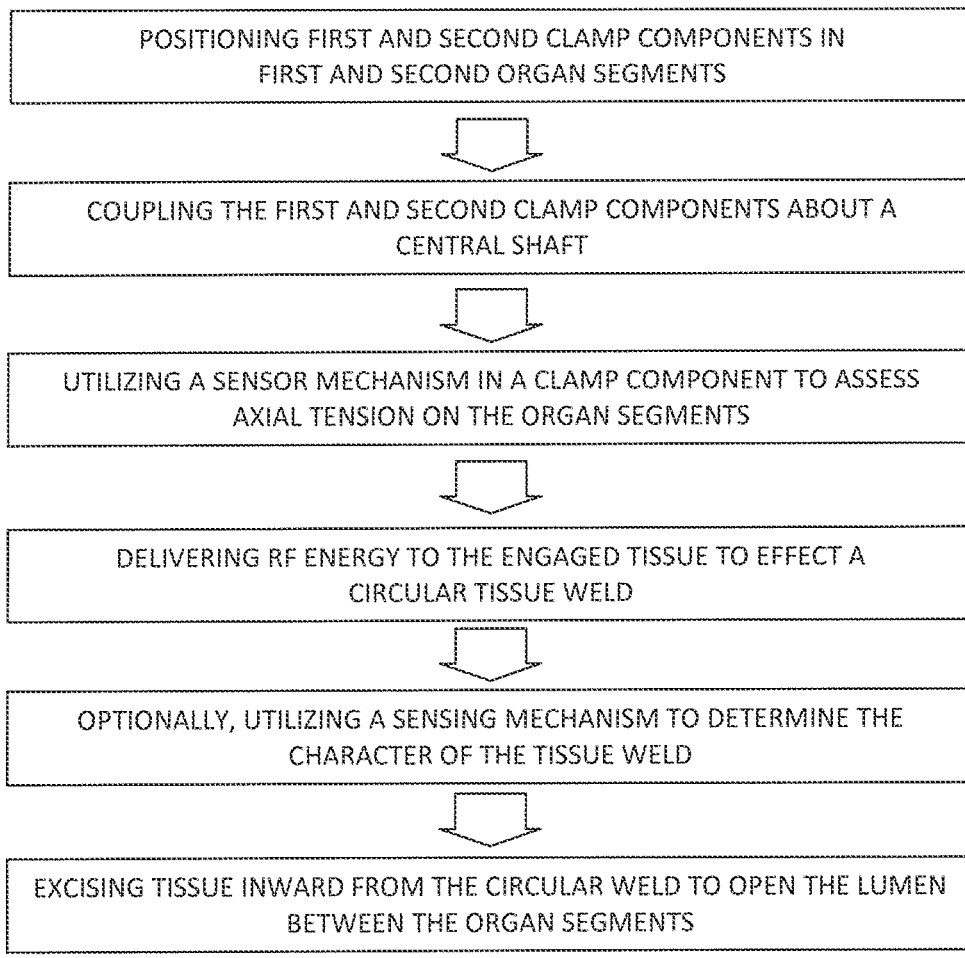
FIG. 14 is a diagram illustrating the steps of a method corresponding to the invention to determine axial tension on organ segments and to thereafter thermally weld together the tubular organ segments.

In general, another method corresponding to the invention shown in FIG. 14 comprises (i) positioning first and second clamp components in first and second organ segments, (ii) coupling the first and second clamp components with a central shaft, (iii) utilizing at least one sensor mechanism in a clamp component to assess axial tension on the organ segments, (iii) if axial tension is acceptable, then delivering RF energy to the engaged tissue to effect a circular tissue weld, (vi) optionally, utilizing a sensing mechanism to determine the character of a tissue weld, and (vii) excising tissue inward from the circular weld to open the lumen between the organ segments.

Figure 15:
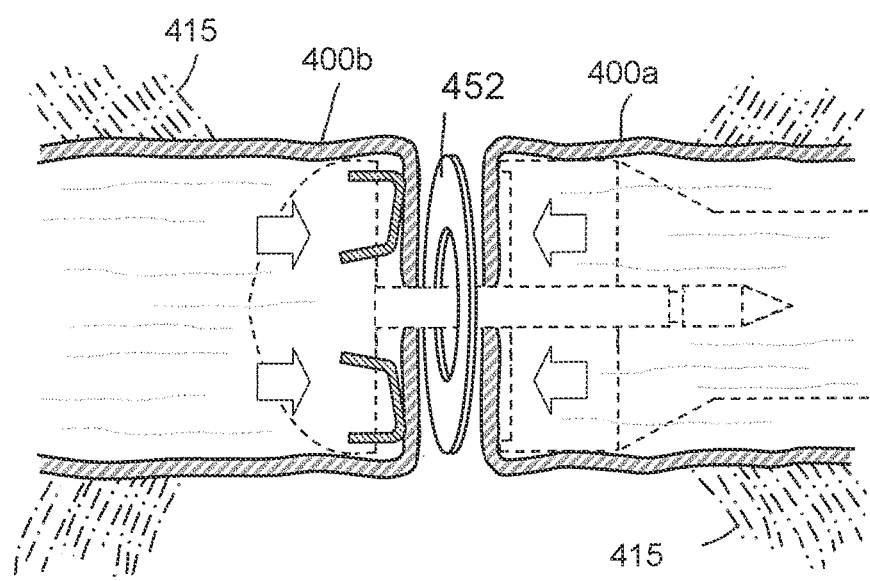
FIG. 15 is a schematic view of a collagen member that can be disposed between surfaces of organ segments to assist in a thermal tissue weld.
Figure 16:
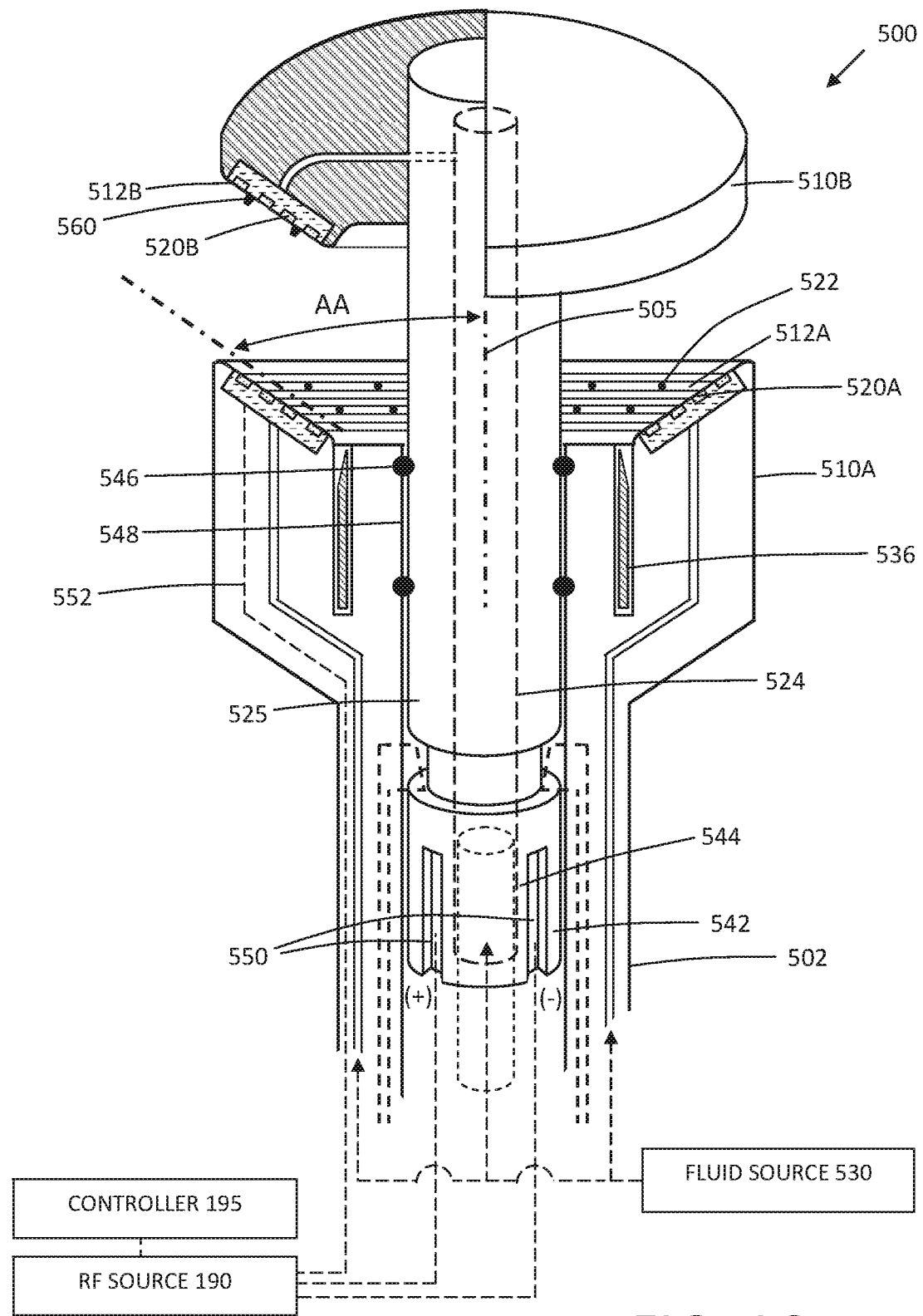
FIG. 16 is a cut-away view of the working end of another variation of a surgical instrument similar to that of FIG. 2.

FIG. 15 illustrates another optional component corresponding to the invention which comprises a thin layer collagen member 452 which may be inserted between the organ segments 400a and 400b and thereby can be clamped between the engaged tissues. The use of such biocompatible collagen material can be used to fuse to the intestinal tissue and potentially strengthen the thermal weld. In one variation, the collagen can be 100% native collagen together with impregnated antimicrobial silver as is known in the art. Such antimicrobial silver can prevent a growth and/or migration of bacteria outwardly from the lumen of the connected segments. In one variation, the collagen member 452 can be of the type manufactured by Medline with a tradename of Puracol Plus AG Collagen Dressing. FIG. 16 illustrates another variation of an electrosurgical anastomosis device 500 which again has an elongate shaft 502 having a central axis 505 which carries first and second clamping components 510A and 510B with first and second respective tissue-engaging faces 512A and 512B configured for clamping together ends of first and second tubular organ segments as described previously. As can be seen in FIG. 16, circular bi-polar electrodes 520A and 520B arrangement are carried in the respective tissue-engaging faces 512A and 512B for thermally welding together tissue of the first and second tubular organ segments. In this variation, a plurality of apertures 522 are carried in both tissue-engaging faces 512A and 512B which communicate with a flow channel 524 in the trocar or shaft portion 525 which is a component of the distal clamping component 510B as described previously. The flow channel 524 in the shaft 525 further communicates with a remote fluid source 530 for providing inflows through apertures 522 which is used to facilitate release of tissue from the electrodes following energy delivery and the creation of the circular weld.

As an example, saline, sterile water or another similar biocompatible fluid can be delivered to the treatment site contemporaneous with release of compression of the welded tissue. The fluid inflow can be pulsed or non-pulsed and can flow at any variable rate at the time an actuation mechanism is used to separate the tissue-engaging faces 512A and 512B.

It should be appreciated that following energy delivery in the welding of the tissue, there remains a possibility of tissue sticking to the electrodes. Thus, the fluid inflow is provided from both sides of the clamping assembly to the engaged tissue to ensure that tissue does not stick to the electrodes. For this reason, the tissue-engaging faces may be separated only slightly over a first-time interval ranging from one second to 30 seconds to infuse the treatment site with fluid. Thereafter, the rate of opening or separating the clamp components from one another can be accomplished at a higher speed.

In one variation, a plurality of apertures 522 ranging from 4 to 100 or more can be provided proximate each electrode arrangement in each tissue-engaging face 512A and 512B to ensure against potential tissue sticking. The surgical device again as a bi-polar electrode arrangement that comprises a plurality of spaced apart circular electrodes of opposing polarities in each tissue-engaging face. A controller is adapted to sense at least one electrical parameter of current delivery to tissue consisting of impedance, capacitance and/or phase angle to sense the thickness of engaged tissue when the first and second clamping components engage tissue. Further, the controller is adapted to sense at least one electrical parameter of current delivery (impedance, capacitance, phase angle) to sense an effective tissue weld to the terminate energy delivery. The controller 195 is further adapted to automatically deliver the fluid inflows from the fluid source 530 after sensing an effective tissue weld. Such fluid inflows can continue for an interval ranging from 1 second to 60 seconds or more.

In one variation, the device further includes a motor drive configured to move together and apart the first and second clamping components 510A and 510B and the controller 195 can be adapted to actuate the motor drive to move apart the first and second clamping components automatically following the termination of energy delivery and initiation of the fluid inflows. In another variation, the controller can be adapted to actuate the motor drive to move apart the first and second clamping components after a predetermined interval of actuating fluid inflows from the fluid source 530, which may be from one second to 20 seconds.

In a variation, the controller 195 is adapted slow or stop actuation of the motor drive to move apart the first and second clamping components 510A and 510B when the controller senses resistance thereto cause by tissue adhering to the bi-polar electrode arrangement, wherein the controller can determine such resistance by monitoring motor voltage required to translate the clamping components 510A and 510B apart at a predetermined rate.

In one variation, the controller 195 is adapted to actuate a motor drive to move a circular cutting member 536 axially from either the first or second clamping component excise tissue inwardly of the first and second tissue-engaging faces.

In another aspect of the invention, referring again to FIG. 16, the first and second clamping components 510A and 510B have first and second respective tissue-engaging faces 512A and 512B that are oriented relative to the central axis 505 at an angle AA ranging from 30° to 85°. More often, the angle AA is 40° to 60°. As can be seen in FIG. 16, bi-polar electrodes are disposed in both the first and second tissue-engaging faces 512A and 512B.

It should be appreciated the cutting mechanism can comprise a mechanical blade 536 that is actuated manually or by a motor drive. Alternatively, the cutting mechanism can comprise an electrosurgical cutting element that again may be moved manually or by a motor drive.

Referring again to FIG. 16, in another aspect of the invention, the central shaft 525 of the second clamping component 510B which is adapted for lockable coupling to the first clamping component 510A includes a flow pathway 524 extending from the apertures 522 therein to a proximal end 542 of the central shaft 525. The proximal end of the central shaft 525 includes a connector portion 544 for fluid-tight connection of the flow pathway to a flow channel in the elongate member that communicates with the fluid source 530. O-rings 546 are provided to seal the space around the shaft 525 in bore 548.

Similarly, the central shaft 525 includes a connector 550 for coupling the electrical conductors 552 in the second clamping component 510B with a cooperating electrical conductors (not shown) in the elongate member which are connected to the RF source 190.

In another aspect of the invention, again referring to FIG. 16, at least one of the first and second tissue-engaging faces 512A and 512B includes a plurality of insulative projecting elements 560 to prevent contact of an electrode in the first face with an electrode in the second face as the clamping components are approximated.

In general, a method of the invention comprises using an electrosurgical device for connecting tubular organ segments so as to communicate with one another, and includes the steps of positioning the walls of a first tubular organ segment around a proximal face of a first clamp component of the device, positioning the walls of a second tubular organ segment around a distal face of a second clamp component of the device, moving together the first and second clamping components thereby clamping together walls of the first and second tubular organ segments, delivering electrosurgical energy between the proximal and distal faces of the clamping components to thereby provide a circular thermal weld in the walls to connect the tubular organ segments, and providing a fluid inflow through apertures in both the proximal face and the distal face to prevent tissue from adhering to the faces. The fluid inflows can be pulsed or non-pulsed.

In another variation of the method of the invention, a biocompatible fluid can be sprayed or otherwise disposed on the electrodes prior to energizing the electrodes to prevent tissue sticking. In one example, biocompatible silicone spray can be used prior to using the device. Other biocompatible fluids and sprays can be used as well for preventing tissue sticking.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method of using an electrosurgical device for connecting tubular organ segments so as to communicate with one another, comprising:
    positioning the walls of a first tubular organ segment around a proximal face of a first clamp component of the device;
    positioning the walls of a second tubular organ segment around a distal face of a second clamp component of the device;
    moving together the first and second clamping components thereby clamping together walls of the first and second tubular organ segments;
    delivering electrosurgical energy between the proximal and distal faces of the clamping components to thereby provide a circular thermal weld in the walls to connect the tubular organ segments; and
    after performing the step of delivering electrosurgical energy between the proximal and the distal faces of the clamping components, removing the first and second clamp components of the device from the first and second tubular organ segments.

2. The method of claim 1 further comprising providing a fluid inflow through apertures in both the proximal face and the distal face to prevent tissue from adhering to the faces.

3. The method of claim 1 wherein the fluid inflow is pulsed.

4. The method of claim 1 wherein the fluid inflow is non-pulsed.

5. The method of claim 1 wherein moving together compresses the thickness of the walls to less than 1.0 mm, less than 0.5 mm, or less than 0.4 mm.

6. The method of claim 1 wherein moving together is motor driven at more than one speed.

7. The method of claim 1 wherein delivering includes multiplexing energy delivery between a plurality of pairs of opposing polarity electrodes in the proximal and distal faces.

8. The method of claim 1 further comprising removing steam from the energy delivery site through a flow pathway in the device.

9. The method of claim 8 wherein the steam escapes passively through the flow pathway.

10. The method of claim 8 wherein the steam is extracted by a negative pressure source.

11. The method of claim 1 further including excising tissue inwardly of the proximal and distal faces to thereby connect the lumens of the first and second tubular organ segments.

12. A method of using an electrosurgical device for connecting tubular organ segments so as to communicate with one another, comprising:
  positioning the walls of a first tubular organ segment around an electrode-carrying face of a first clamp component, wherein the face is coated with a biocompatible fluid for preventing tissue adherence thereto;
  positioning the walls of a second tubular organ segment around an electrode carrying face of a second clamp component, wherein the face is coated with a biocompatible fluid for preventing tissue adherence thereto;
  moving together the first and second clamping components thereby clamping together walls of the first and second tubular organ segments;
  delivering electrosurgical energy between the proximal and distal faces of the clamping components to thereby provide a circular thermal weld in the walls to connect the tubular organ segments; and
  after performing the step of delivering electrosurgical energy between the proximal and distal faces of the clamping components, removing the first and second clamp components from the first and second tubular organ segments.

* * * * *